(12) United States Patent
Nakagami et al.

(10) Patent No.: US 10,695,420 B2
(45) Date of Patent: Jun. 30, 2020

(54) DNA-PEPTIDE COMBINATION VACCINE

(71) Applicants: ANGES, INC., Ibaraki-shi, Osaka (JP); OSAKA UNIVERSITY, Suita-shi, Osaka (JP); DS PHARMA ANIMAL HEALTH CO., LTD., Osaka-shi, Osaka (JP)

(72) Inventors: Hironori Nakagami, Suita (JP); Ryuichi Morishita, Suita (JP); Hiroshi Koriyama, Suita (JP); Hideki Tomioka, Ibaraki (JP); Kenji Naohara, Osaka (JP)

(73) Assignees: ANGES, INC., Ibaraki (JP); OSAKA UNIVERSITY, Suita (JP); DS PHARMA ANIMAL HEALTH CO., LTD., Osaka (JP)

( * ) Notice: Subject to any disclaimer, the term of this patent is extended or adjusted under 35 U.S.C. 154(b) by 0 days.

(21) Appl. No.: 15/528,502

(22) PCT Filed: Nov. 20, 2015

(86) PCT No.: PCT/JP2015/082778
§ 371 (c)(1),
(2) Date: May 20, 2017

(87) PCT Pub. No.: WO2016/080540
PCT Pub. Date: May 26, 2016

(65) Prior Publication Data
US 2017/0258895 A1 Sep. 14, 2017

(30) Foreign Application Priority Data
Nov. 20, 2014 (JP) ................. 2014-235736

(51) Int. Cl.
*A61K 39/00* (2006.01)
*A61K 39/29* (2006.01)
*C12N 7/00* (2006.01)

(52) U.S. Cl.
CPC ........ *A61K 39/292* (2013.01); *A61K 39/0008* (2013.01); *C12N 7/00* (2013.01); *A61K 2039/53* (2013.01); *A61K 2039/545* (2013.01); *A61K 2039/70* (2013.01); *C12N 2730/10134* (2013.01)

(58) Field of Classification Search
None
See application file for complete search history.

(56) References Cited

U.S. PATENT DOCUMENTS

| 2003/0175296 A1 | 9/2003 | Brown et al. |
| 2014/0086944 A1 | 3/2014 | Kyutoku et al. |
| 2014/0099335 A1 | 4/2014 | Morishita et al. |
| 2015/0202271 A1 | 7/2015 | Nakagami et al. |

FOREIGN PATENT DOCUMENTS

| JP | H03-216186 A | 9/1991 |
| JP | 2004-307477 A | 11/2004 |
| JP | 2014-060968 A | 4/2014 |
| WO | WO 2012/141280 A1 | 10/2012 |
| WO | WO 2014/034735 A1 | 3/2014 |

OTHER PUBLICATIONS

Chen et al. Enhanced Effect of DNA Immunization plus In Vivo Electroporation with a Combination of Hepatitis B Virus Core-PreS1 and S-PreS1 Plasmids. Clinical and Vaccine Immunology, Nov. 2011, vol. 18, No. 11, p. 1789-1795.*
Bertino et al. A Comparative Trial of Standard or High-Dose S Subunit Recombinant Hepatitis B Vaccine versus a Vaccine Containing S Subunit, Pre-Sj, and Pre-S2 Particles for Revaccination of Healthy Adult Nonresponders. The Journal of Infectious Diseases 1997;175:678-81.*
Yang et al. Protective immune response induced by co-immunization with the Trichinella spiralis recombinant Ts87 protein and a Ts87 DNA vaccine. Veterinary Parasitology 194 (2013) 207-210.*
Li et al. HIV/SIV DNA vaccine combined with protein in a co-immunization protocol elicits highest humoral responses to envelope in mice and macaques.Vaccine 31 (2013) 3747-3755.*
Ambubl et al. A vaccine for hypertension based on virus-like particles: preclinical efficacy and phase I safety and immunogenicity. J Hypertens 2007, 25:63-72.*
Koriyama et al. 736. DNA Vaccine for High Blood Pressure—Anti-Angiotensin II Therapy in Spontaneously Hypertensive Rats. Molecular Therapy vol. 19, Supplement 1, May 2011, S281-282.*
Kafi et al. Maleimide conjugation markedly enhances the immunogenicity of both human and murine idiotype-KLH vaccines. Mol Immunol. Jan. 2009;46(3):448-56. Epub Nov. 28, 2008.*
Cruz et al. Enhanced immunogenicity and cross-reactivity of HIV-1 V3-peptide and multiple antigen peptides conjugated to distinct carrier proteins. Int Immunopharmacol. Nov. 2009;9(12):1452-9. Epub Sep. 10, 2009.*
Kwissa et al. Codelivery of a DNA vaccine and a protein vaccine with aluminum phosphate stimulates a potent and multivalent immune response. J Mol Med (2003) 81:502-510.*
Cayabyab et al., "Robust immune response elicited by a novel and unique *Mycobacterium tuberculosis* protein using an optimized DNA/protein heterologous prime/boost protocol," *Immunology*, 135(3): 216-225 (2012).

(Continued)

*Primary Examiner* — Nianxiang Zou
(74) *Attorney, Agent, or Firm* — Leydig, Voit & Mayer, Ltd.

(57) ABSTRACT

The present invention provides a combination preparation for inducing a specific immune response to an antigenic peptide, which contains
(I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide, wherein the antigenic peptide of (I) and the expression vector of (II) are substantially simultaneously administered to a subject.

14 Claims, 22 Drawing Sheets
Specification includes a Sequence Listing.

(56) References Cited

OTHER PUBLICATIONS

Dar et al., "DNA prime-protein boost strategy with replicase-based DNA vaccine against foot-and-mouth disease in bovine calves," *Vet. Microbiol.*, 163(1-2): 62-70 (2013).
Felber et al., "HIV DNA Vaccine: Stepwise Improvements Make a Difference," *Vaccines* (Basel), 2(2): 354-379 (2014).
Fowler et al., "A DNA vaccination regime including protein boost and electroporation protects cattle against foot-and-mouth disease," *Antiviral Res.*, 94(1): 25-34 (2012).
Ishikawa et al., "Co-immunization with West Nile DNA and inactivated vaccines provides synergistic increases in their immunogenicities in mice," *Microbes. Infect.*, 9(9): 1089-1095 (2007).
Kyutoku et al., "Development of novel DNA vaccine for VEGF in murine cancer model," *Sci. Rep.*, 3: 3380 (2013).
Kyutoku et al., "Inhibition of Neointima Formation through DNA Vaccination for Apolipoprotein(a): A New Therapeutic Strategy for Lipoprotein(a)," *Sci. Rep.*, 3: 1600 (2013).
Mehrizi et al., "Immune responses elicited by co-immunization of *Plasmodium vivax* and *P. falciparum* MSP-1 using prime-boost immunization strategies," *Parasite Immunol.*, 33(11): 594-608 (2011).
Nakagami et al., "Therapeutic Vaccines for Hypertension and Dyslipidemia," *Int. Heart J.*, 55(2): 96-100 (2014).
Yang et al., "Protective immune response induced by co-immunization with the *Trichinella spiralis* recombinant Ts87 protein and a Ts87 DNA vaccine," *Vet. Parasitol.*, 194(2-4): 207-210 (2013).
Japanese Patent Office, International Search Report in International Application No. PCT/JP2015/082778 (dated Feb. 9, 2016).
Laing et al., "The 'Co-Delivery' Approach to Liposomal Vaccines: Application to the Development of influenza-A and hepatitis-B Vaccine Candidates," *J. Liposome Res.*, 16(3): 229-235 (2006).
European Patent Office, Extended European Search Report in European Patent Application No. 15861370.3 (dated Jun. 4, 2018).

* cited by examiner

SEQUENCE LISTING

```
<160> NUMBER OF SEQ ID NOS: 40

<210> SEQ ID NO 1
<211> LENGTH: 13
<212> TYPE: PRT
<213> ORGANISM: Artificial Sequence
<220> FEATURE:
<223> OTHER INFORMATION: Synthetic partial peptide of mouse VEGF-A

<400> SEQUENCE: 1

Ile Met Arg Ile Lys Pro His Gln Ser Gln His Ile Gly
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic partial peptide of mouse VEGF-A

<400> SEQUENCE: 2

Met Arg Ile Lys Pro His Gln
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic partial peptide of mouse VEGF-A

<400> SEQUENCE: 3

Met Gln Ile Met Arg Ile Lys Pro His Gln Ser Gln His Ile Gly Glu
1               5                   10                  15

Met

<210> SEQ ID NO 4
<211> LENGTH: 13
<212> TYPE: PRT
<213> ORGANISM: Artificial Sequence
<220> FEATURE:
<223> OTHER INFORMATION: Synthetic partial peptide of human VEGF-A

<400> SEQUENCE: 4
```

```
Ile Met Arg Ile Lys Pro His Gln Gly Gln His Ile Gly
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Synthetic partial peptide of human VEGF-A

<400> SEQUENCE: 5

```
Met Arg Ile Lys Pro His Gln
1               5
```

<210> SEQ ID NO 6
<211> LENGTH: 17
<212> TYPE: PRT
<213> ORGANISM: Artificial Sequence
<220> FEATURE:
<223> OTHER INFORMATION: Synthetic partial peptide of human VEGF-A

<400> SEQUENCE: 6

```
Met Gln Ile Met Arg Ile Lys Pro His Gln Gly Gln His Ile Gly Glu
1               5                   10                  15

Met
```

<210> SEQ ID NO 7
<211> LENGTH: 16
<212> TYPE: PRT
<213> ORGANISM: Artificial Sequence
<220> FEATURE:
<223> OTHER INFORMATION: Synthetic partial peptide of human
      angiopoietin-2

<400> SEQUENCE: 7

```
Pro Gln Arg Gln Asn Thr Asn Lys Phe Asn Gly Ile Lys Trp Tyr Tyr
1               5                   10                  15
```

<210> SEQ ID NO 8
<211> LENGTH: 11
<212> TYPE: PRT
<213> ORGANISM: Artificial Sequence
<220> FEATURE:
<223> OTHER INFORMATION: Synthetic partial peptide of human
      angiopoietin-2

<400> SEQUENCE: 8

```
Tyr Tyr Pro Gln Arg Gln Asn Thr Asn Lys Glu
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: Synthetic partial peptide of human angiotensin
      II

<400> SEQUENCE: 9

```
Cys Gly Gly Asp Arg Val Tyr Ile His Pro Phe
1               5                   10
```

<210> SEQ ID NO 10
<211> LENGTH: 13
<212> TYPE: PRT
<213> ORGANISM: Artificial Sequence

```
<220> FEATURE:
<223> OTHER INFORMATION: Synthetic partial peptide of human angiotensin
      II

<400> SEQUENCE: 10

Cys Gly Gly Asp Arg Val Tyr Ile His Pro Phe His Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic partial peptide of human angiotensin
      II

<400> SEQUENCE: 11

Asp Arg Val Tyr Ile His Pro Phe His Leu Gly Gly Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic partial peptide of human angiotensin
      II

<400> SEQUENCE: 12

Cys Asp Arg Val Tyr Ile His Pro Phe His Leu
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 13

Cys His Pro Phe His Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 14

Cys Gly Pro Phe His Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 15

Cys Tyr Ile His Pro Phe
1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 16

Cys Gly Ile His Pro Phe
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 17

Cys Gly Gly His Pro Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic partial peptide of human angiotensin
      II

<400> SEQUENCE: 18

Cys Arg Val Tyr Ile Gly Gly Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic partial peptide of human angiotensin
      II

<400> SEQUENCE: 19

Asp Arg Val Tyr Gly Gly Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic partial peptide of human angiotensin
      II

<400> SEQUENCE: 20

Asp Arg Val Gly Gly Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic partial peptide of human angiotensin
      II
```

```
<400> SEQUENCE: 21

Asp Arg Val Tyr Ile His Pro Phe
1               5

<210> SEQ ID NO 22
<211> LENGTH: 25
<212> TYPE: PRT
<213> ORGANISM: Artificial Sequence
<220> FEATURE:
<223> OTHER INFORMATION: Synthetic partial peptide of human, mouse or
      rabbit CETP

<400> SEQUENCE: 22

Arg Asp Gly Phe Leu Leu Leu Gln Met Asp Phe Gly Phe Pro Glu His
1               5                   10                  15

Leu Leu Val Asp Phe Leu Gln Ser Leu
            20                  25

<210> SEQ ID NO 23
<211> LENGTH: 12
<212> TYPE: PRT
<213> ORGANISM: Artificial Sequence
<220> FEATURE:
<223> OTHER INFORMATION: Synthetic partial peptide of human
      apolipoprotein(a)

<400> SEQUENCE: 23

Glu Ala Pro Ser Glu Gln Ala Pro Thr Glu Gln Arg
1               5                   10

<210> SEQ ID NO 24
<211> LENGTH: 183
<212> TYPE: PRT
<213> ORGANISM: Hepatitis B virus

<400> SEQUENCE: 24

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 25
<211> LENGTH: 185
<212> TYPE: PRT
<213> ORGANISM: Hepatitis B virus

<400> SEQUENCE: 25

Met Asp Ile Asp Pro Tyr Lys Glu Phe Gly Ala Thr Val Glu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 26
<211> LENGTH: 22
<212> TYPE: DNA
<213> ORGANISM: Artificial Sequence
<220> FEATURE:
<223> OTHER INFORMATION: Synthetic immune-stimulating CpG sequence

<400> SEQUENCE: 26
tgactgtgaa cgttcgagat ga                                          22

<210> SEQ ID NO 27
<211> LENGTH: 20
<212> TYPE: DNA
<213> ORGANISM: Artificial Sequence
<220> FEATURE:
<223> OTHER INFORMATION: Synthetic immune-stimulating CpG sequence

<400> SEQUENCE: 27
ggtgcatcga tgcagggggg                                             20

<210> SEQ ID NO 28
<211> LENGTH: 21
<212> TYPE: DNA
<213> ORGANISM: Artificial Sequence
<220> FEATURE:
<223> OTHER INFORMATION: Synthetic immune-stimulating CpG sequence

<400> SEQUENCE: 28

```
tcgtcgaacg ttcgagatga t                                              21
```

<210> SEQ ID NO 29
<211> LENGTH: 25
<212> TYPE: DNA
<213> ORGANISM: Artificial Sequence
<220> FEATURE:
<223> OTHER INFORMATION: Synthetic immune-stimulating CpG sequence

<400> SEQUENCE: 29

```
tcgaacgttc gaacgttcga acgtt                                          25
```

<210> SEQ ID NO 30
<211> LENGTH: 88
<212> TYPE: DNA
<213> ORGANISM: Artificial Sequence
<220> FEATURE:
<223> OTHER INFORMATION: Synthetic immune-stimulating CpG sequence

<400> SEQUENCE: 30

```
ggtgcatcga tgcagggggg tgactgtgaa cgttcgagat gatcgtcgaa cgttcgagat    60
gattcgaacg ttcgaacgtt cgaacgtt                                       88
```

<210> SEQ ID NO 31
<211> LENGTH: 24
<212> TYPE: DNA
<213> ORGANISM: Artificial Sequence
<220> FEATURE:
<223> OTHER INFORMATION: Synthetic CpG oligonucleotide

<400> SEQUENCE: 31

```
tcgtcgtttt gtcgttttct cgtt                                           24
```

<210> SEQ ID NO 32
<211> LENGTH: 21
<212> TYPE: DNA
<213> ORGANISM: Artificial Sequence
<220> FEATURE:
<223> OTHER INFORMATION: Synthetic CpG oligonucleotide

<400> SEQUENCE: 32

```
tcgtcgttaa cgttaacgct a                                              21
```

<210> SEQ ID NO 33
<211> LENGTH: 12
<212> TYPE: PRT
<213> ORGANISM: Artificial Sequence
<220> FEATURE:
<223> OTHER INFORMATION: Synthetic partial peptide of mouse DPP4

<400> SEQUENCE: 33

```
Ser Lys Asp Glu Ala Ala Ala Asp Ser Arg Arg Thr
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: Synthetic partial peptide of mouse DPP4

<400> SEQUENCE: 34

```
Lys Ser Thr Phe Arg Val Lys Ser Tyr Ser
1               5                   10
```

```
<210> SEQ ID NO 35
<211> LENGTH: 9
<212> TYPE: PRT
<213> ORGANISM: Artificial Sequence
<220> FEATURE:
<223> OTHER INFORMATION: Synthetic partial peptide of mouse DPP4

<400> SEQUENCE: 35

Glu Asn Ser Thr Phe Glu Ser Phe Gly
1               5

<210> SEQ ID NO 36
<211> LENGTH: 11
<212> TYPE: PRT
<213> ORGANISM: Artificial Sequence
<220> FEATURE:
<223> OTHER INFORMATION: Synthetic partial peptide of mouse IL-17

<400> SEQUENCE: 36

Ser Ser Ala Cys Pro Asn Thr Glu Ala Lys Asp
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic partial peptide of mouse IL-17

<400> SEQUENCE: 37

Lys Val Ser Ser Arg Arg Pro Ser Asp Tyr Leu Asn Arg Ser Thr Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic partial peptide of mouse IL-17

<400> SEQUENCE: 38

His Arg Asn Glu Asp Pro Asp Arg Tyr Pro Ser Val Ile Trp Glu
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: Synthetic partial peptide of mouse IL-17

<400> SEQUENCE: 39

Lys Arg Glu Pro Glu Ser Cys Pro Phe Thr
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic partial peptide of mouse IL-17

<400> SEQUENCE: 40

Glu Lys Met Leu Val Gly Val Gly Cys Thr Cys Val Ala Ser Ile
1               5                   10                  15
```

DNA-PEPTIDE COMBINATION VACCINE

CROSS-REFERENCE TO RELATED APPLICATIONS

This patent application is the U.S. national phase of International Patent Application No. PCT/JP2015/082778, filed Nov. 20, 2015, which claims the benefit of Japanese Patent Application No. 2014-235736, filed on Nov. 20, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,511 bytes ASCII (Text) file named "728823 Sequence-Listing.txt," created May 19, 2017.

TECHNICAL FIELD

The present invention relates to a preparation for inducing a specific immune response to an antigenic peptide.

BACKGROUND ART

A vaccine therapy has been proposed in which an immune response to an autoantigen in vivo is positively induced to neutralize the activity of the autoantigen, whereby a disease to which the autoantigen contributes is prevented or treated.

The present inventors have reported that hypertension can be treated well by inducing production of an antibody against angiotensin II, which is achieved by conjugating an angiotensin II-specific epitope with KLH and administering the conjugate (non-patent document 1). Also, the present inventors have found that administration of an expression vector encoding a chimeric hepatitis B virus core antigen polypeptide, wherein an angiotensin II-specific epitope is inserted between amino acid residues 80 and 81 of hepatitis B virus core antigen polypeptide, induces antibody production against angiotensin II and can favorably treat or prevent lifestyle-related diseases such as hypertension and the like (patent document 1). In addition, they have found that administration of an expression vector encoding a chimeric hepatitis B virus core antigen polypeptide, wherein an apolipoprotein (a)-specific epitope is inserted between amino acid residues 80 and 81 of hepatitis B virus core antigen polypeptide, induces antibody production against apolipoprotein (a) while avoiding self-reactive T cell induction and can favorably treat or prevent arteriosclerosis (patent document 2, non-patent document 2). Furthermore, they have found that administration of an expression vector encoding a chimeric hepatitis B virus core antigen polypeptide, wherein a VEGF-specific epitope and/or an angiopoietin-2-specific epitope are/is inserted between amino acid residues 80 and 81 of hepatitis B virus core antigen polypeptide, effectively suppresses tumor angiogenesis, and can treat or prevent cancer (patent document 3, non-patent document 3).

As for DNA vaccine using an expression vector encoding an antigen, it has been reported that boosting by administration of the antigen itself after administration of the DNA vaccine enhances the vaccine effect (non-patent documents 4-7).

However, such effectiveness of these vaccines is not sufficiently satisfactory.

DOCUMENT LIST

Patent Documents

[patent document 1] WO 2012/141280 A1
[patent document 2] JP 2014-60968 A
[patent document 3] WO 2014/034735 A1

Non-Patent Document

[non-patent document 1] Int Heart J. 2014; 55(2):96-100
[non-patent document 2] Kyutoku M, Nakagami H, Koriyama H, Nakagami F, Shimamura M, Kurinami H, Tomioka H, Miyake T, Katsuya T, Morishita R. Inhibition of Neointima Formation through DNA Vaccination for Apolipoprotein (a): A New Therapeutic Strategy for Lipoprotein (a). Sci Rep. 2013 Apr. 3; 3:1600
[non-patent document 3] Kyutoku M, Nakagami H, Koriyama H, Tomioka H, Nakagami F, Shimamura M, Kurinami H, Zhengda P, Jo D H, Kim J H, Takakura N, Morishita R. Development of novel DNA vaccine for VEGF in murine cancer model. Sci Rep. 2013 Nov. 29; 3:3380
[non-patent document 4] Parasite Immunol. 2011 November; 33(11):594-608
[non-patent document 5] Immunology. 2012 March; 135(3): 216-25
[non-patent document 6] Vet Microbiol. 2013 Apr. 12; 163(1-2):62-70
[non-patent document 7] Antiviral Res. 2012 April; 94(1): 25-34

SUMMARY OF THE INVENTION

Problems to be Solved by the Invention

To increase introduction efficiency of DNA vaccines, electroporation and nucleic acid introduction reagents are sometimes used in combination. Such treatments require special administration device, apparatus, reagents and the like, which may impose economic burden on patients since the treatment costs increase. In addition, treatments such as electroporation and the like and multiple repeated administrations of vaccine place physical burden on the subject of administration. Thus, the development of a technique for reducing these economical and physical burdens is desired.

Accordingly, the present invention aims to provide a DNA vaccine technique capable of effectively inducing a specific immune response to antigen, which does not require a treatment such as electroporation, nucleic acid introduction reagent and the like.

Means of Solving the Problems

The present inventors have found as a result of intensive studies that simultaneous administration of an expression vector encoding a chimeric hepatitis B virus core antigen polypeptide, into which an antigenic peptide has been inserted, with the antigenic peptide itself strongly induces an antibody specific to said antigenic peptide. Such simultaneous combined use of DNA vaccine and peptide vaccine could strongly induce specific antibody against antigenic peptide, even without requiring electroporation and nucleic acid introduction reagent. Also, due to simultaneous combined use of DNA vaccine and peptide vaccine, an increase in the titer of antibody specific to the antigenic peptide lasted for a long term as compared to single administration. Furthermore, simultaneous combined use of DNA vaccine and peptide vaccine preferentially induced IgG rather than IgM. Based on these findings, further studies have been conducted and the present invention was completed.

That is, the present invention relates to the following.

[1] A combination preparation for inducing a specific immune response to an antigenic peptide, which comprises
(I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide, wherein the antigenic peptide of (I) and the expression vector of (II) are substantially simultaneously administered to a subject.

[2] The preparation of [1], wherein, in the chimeric hepatitis B virus core antigen polypeptide, the antigenic peptide is inserted between the amino acid residues 80 and 81 of the hepatitis B virus core antigen polypeptide.

[3] The preparation of [1] or [2], which is formulated as a single preparation.

[4] The preparation of any of [1]-[3], wherein the peptide of (I) and the expression vector of (II) are administered to the subject by the same administration route.

[5] The preparation of [4], which is administered subcutaneously, intradermally, or intramuscularly.

[6] The preparation of any of [1]-[5], wherein the number of administrations is one.

[7] The preparation of any of [1]-[6], which does not use electroporation and/or a nucleic acid introduction reagent for administration.

[8] The preparation of any of [1]-[7], which is free of an adjuvant.

[9] The preparation of any of [1]-[8], wherein the antigenic peptide is an autoantigen protein of the subject or a partial peptide thereof.

[10] The preparation of [9], wherein the autoantigen protein is an antigen that contributes to the exacerbation of a disease.

[11] The preparation of [10], wherein the disease is a lifestyle-related disease.

[12] The preparation of [10] or [11], wherein the autoantigen protein is angiotensin II.

[13] The preparation of [12], which is for the treatment or prophylaxis of cardiac failure, hypertension, renal failure, arteriosclerosis, myocardial infarction, cerebral infarction, arteriosclerosis obliterans, or dementia.

[14] The preparation of [13], which is for the treatment or prophylaxis of cardiac failure caused by mitral insufficiency.

[15] The preparation of [10] or [11], wherein the autoantigen protein is VEGF.

[16] The preparation of [15], which is for the treatment or prophylaxis of cancer, diabetic retinopathy, age-related macular degeneration, or retinopathy of prematurity.

[17] The preparation of any of [1]-[16], wherein the subject is human.

[18] The preparation of any of [1]-[16], wherein the subject is a non-human mammal.

[19] A method of inducing a specific immune response to an antigenic peptide in a subject, which comprises substantially simultaneously administering
(I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide.

[20] A combination for use for the induction of a specific immune response to an antigenic peptide, which comprises
(I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide, wherein the antigenic peptide of (I) and the expression vector of (II) are substantially simultaneously administered to a subject.

[21] Use of a combination in the production of a medicament for inducing a specific immune response to an antigenic peptide, which combination comprises
(I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide, wherein the antigenic peptide of (I) and the expression vector of (II) are substantially simultaneously administered to a subject.

Effect of the Invention

According to the present invention, a vaccine capable of strongly inducing a specific antibody against an antigenic peptide can be provided.

According to the present invention, a specific antibody against an antigenic peptide can be effectively induced using a DNA vaccine, without requiring a treatment such as electroporation, nucleic acid introduction reagent and the like.

According to the present invention, moreover, since an increase in the titer of antibody specific to the antigenic peptide lasts for a long term, the number of vaccine administrations can be reduced.

BRIEF DESCRIPTION OF THE DRAWINGS

FIG. 12-1 shows an increase in the antibody titer by the administration of a DNA-peptide combination vaccine (2W and 4W), wherein the vertical axis shows absorbance by ELISA, and the horizontal axis shows dilution rate of serum.

FIG. 12-2 shows an increase in the antibody titer by the administration of a DNA-peptide combination vaccine (8W and 12W), wherein the vertical axis shows absorbance by ELISA, and the horizontal axis shows dilution rate of serum.

FIG. 13-1 shows an increase in the antibody titer by the administration of a DNA-peptide combination vaccine (2W), wherein the vertical axis shows absorbance by ELISA, and the horizontal axis shows dilution rate of serum.

FIG. 13-2 shows an increase in the antibody titer by the administration of a DNA-peptide combination vaccine (2W). A 250-fold diluted serum was used. The vertical axis shows absorbance by ELISA. mean±S.D. (n=6). *p<0.01 (relative to the same dose of angiotensin II vaccine-1).

FIG. 14-1 shows an increase in the antibody titer by the administration of a DNA-peptide combination vaccine (4W), wherein the vertical axis shows absorbance by ELISA, and the horizontal axis shows dilution rate of serum.

FIG. 14-2 shows an increase in the antibody titer by the administration of a DNA-peptide combination vaccine (4W). A 250-fold diluted serum was used. The vertical axis shows absorbance by ELISA. mean±S.D. (n=6). *p<0.01 (relative to the same dose of angiotensin II vaccine-1).

FIG. 16-1 shows the profile of systolic blood pressure and heart rate of individual No. 1.

FIG. 16-2 shows the profile of systolic blood pressure and heart rate of individual No. 2.

FIG. 16-3 shows the profile of systolic blood pressure and heart rate of individual No. 3.

DESCRIPTION OF EMBODIMENTS

Figure 1:
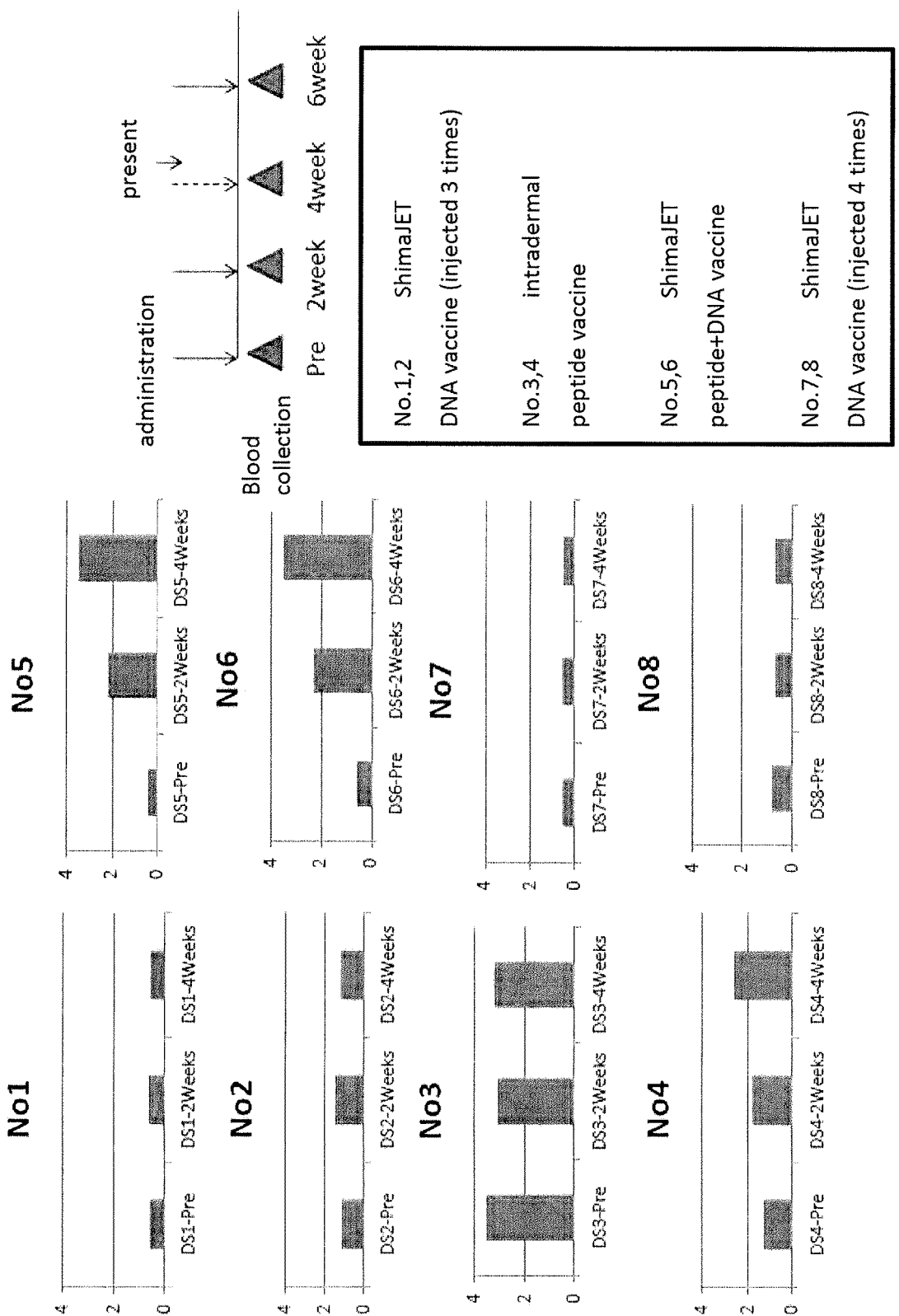
FIG. 1 shows an increase in the antibody titer to angiotensin II by the administration of a DNA-peptide combination vaccine.

The present invention provides a combination preparation for inducing a specific immune response to an antigenic peptide, which comprises (I) the antigenic peptide, and
(II) an expression vector encoding a chimeric hepatitis B virus core antigen polypeptide, into which the antigenic peptide has been inserted or added, wherein said antigenic peptide is inserted in a region of amino acid residues 74-87 or 130-138 of the hepatitis B virus core antigen polypeptide, or added to the N-terminal or C-terminal of the hepatitis B virus core antigen polypeptide.

Antigenic peptide refers to a peptide recognized by the immune system of a subject of administration, and having an activity to induce an immune response specific to the peptide, preferably, a humoral immune response specific to the peptide (i.e., production of antibody that specifically recognizes the peptide).

"Specific recognition" of antigen X by antibody means that the binding affinity of the antibody to antigen X in an antigen-antibody reaction is higher than that to a non-specific antigen (e.g., BSA).

The kind of the antigenic peptide to be used in the present invention is not particularly limited as long as it has antigenicity. Preferred is an autoantigen protein of a subject to whom the preparation of the present invention is applied, or a partial peptide thereof. In the present invention, an expression vector encoding a chimeric hepatitis B virus core (HBc) antigen polypeptide, into which the antigenic peptide has been inserted, wherein said antigenic peptide is inserted between the amino acid residues 80 and 81 of the hepatitis B virus core antigen polypeptide is used. HBc antigen protein constitutes a spherical core particle by self-assembly. The core particle has very high immunogenicity. When a desired peptide is inserted between the amino acid residues 80 and 81 of the HBc antigen protein, the peptide is presented on the surface of the particles formed by self-assembly. Using the chimeric HBc antigen polypeptide, the inserted epitope is easily recognized by an immune system, and the production of an antibody that specifically recognizes the peptide can be efficiently induced. Therefore, utilizing the HBc antigen protein as a platform of vaccine makes it possible to induce even production of an antibody against an autoantigen protein or a partial peptide thereof that is difficult to be recognized by an immune system (D. C. Whitacre et al., Expert Rev. Vaccines, vol.8, no.11, pp.1565-1573, 2009; B. E. Clarke et al., Nature, vol.330, pp.381-384, 1987; JP-B-3228737).

Autoantigen protein means an antigen protein encoded on a gene of a subject animal itself to whom the preparation of the present invention is applied. The application subject of the preparation of the present invention is a mammal. Examples of the mammal include rodents such as mouse, rat, hamster, guinea pig and the like, lagomorphas such as rabbit and the like, ungulates such as swine, bovine, goat, horse, sheep and the like, carnivore such as dog, cat and the like, primates such as human, monkey, Macaca mulatta, Macaca fascicularis, marmoset, orangutan, chimpanzee and the like, and the like. The mammal is preferably a carnivore (dog, cat etc.) or a primate (human etc.). Therefore, for example, when the preparation of the present invention is applied to human, use of human autoantigen protein or a partial peptide thereof is preferably intended, but is not limited thereto. In addition, when the preparation of the present invention is applied to dog, use of an autoantigen protein of the dog or a partial peptide thereof is preferably intended, but is not limited thereto. Furthermore, when the preparation of the present invention is applied to cat, use of an autoantigen protein of the cat or a partial peptide thereof is preferably intended, but is not limited thereto.

In the present specification, regarding the particular factor X (polypeptide or polynucleotide), "factor X derived from organism Y" or "organism Y factor X" means that the amino acid sequence or nucleic acid sequence of factor X has the same amino acid sequence or nucleic acid sequence as the amino acid sequence or nucleic acid sequence of factor X naturally expressed in organism Y.

The kind of the autoantigen protein is not particularly limited. In one embodiment, it is an antigen that contributes to the exacerbation of a disease. In this embodiment, when the preparation of the present invention is administered to a subject, an immune response specific to the autoantigen protein or a partial peptide thereof, preferably, a humoral immune response specific to the peptide (i.e., production of antibody that specifically recognizes the peptide), is induced, and the activity of the autoantigen protein is neutralized by the antibody, whereby the disease exacerbated by the involvement of the autoantigen protein can be prevented or treated.

In one embodiment, an autoantigen protein is an antigen that contributes to the exacerbation of a lifestyle-related disease (a lifestyle-related disease-associated factor). In the present specification, the lifestyle-related disease is a generic term of the diseases caused by lifestyle such as dietary habits, exercise habits, rest, smoking, alcohol drinking and the like. Examples of the lifestyle-related disease include hypertension, hyperlipidemia, diabetes, insulin resistance, arteriosclerosis (arteriosclerosis obliterans etc.), ischemic disease (myocardial infarction, cerebral apoplexy etc.), obesity, diabetic retinopathy, high LDLemia and the like. In the preparation of the present invention, by using a lifestyle-related disease-associated factor or a partial peptide thereof as an antigenic peptide, the lifestyle-related disease can be treated or ameliorated by inducing production of an antibody to a lifestyle-related disease-associated factor and neutralizing the lifestyle-related disease-associated factor by the antibody.

In one embodiment, the autoantigen protein is a humoral factor. Using a humoral factor protein as an autoantigen protein, rather than an intracellular protein or cellular surface protein, humoral immunity to the humoral factor is predominantly induced, and the activity of the humoral factor can be effectively neutralized while avoiding an adverse influence of the induced immunity (cellular immunity and humoral immunity, particularly cellular immunity) on normal tissues.

While autoantigen protein as a humoral factor that contributes to the exacerbation of a disease (e.g., lifestyle-related disease) is not particularly limited, for example, angiotensin II, angiotensin I, ACE, renin, cholesteryl ester transfer protein (CETP), VEGF (VEGF-A, B, C, D or E, PLGF-1, or PLGF-2), angiopoietin-2, apolipoprotein (a), proprotein convertase subtilisin/kexin type 9 (PCSK9), DPP4 (Dipeptidyl Peptidase-4), IL-17 (interleukin17) and the like can be mentioned. Angiotensin II, angiotensin I, ACE and renin contribute to the exacerbation of cardiac failure, hypertension, hyperlipidemia, and renal failure. CETP contributes to the exacerbation of hyperlipidemia. VEGF and angiopoietin-2 promote tumor angiogenesis, and contribute to the exacerbation of cancer (particularly solid tumor). Apolipoprotein (a) contributes to the exacerbation of arteriosclerosis (particularly, atherosclerosis). PCSK9 is involved in high LDLemia. DPP4 is involved in diabetes and insulin resistance. IL-17 is involved in autoimmune diseases and inflammatory diseases such as rheumatism, SLE, ulcerative colitis and the like, and cancer.

The size of the antigenic peptide to be used in the present invention is generally 5-30 amino acids, preferably 6-25 amino acids, more preferably 10-18 amino acids, furthermore preferably 11-16 amino acids. When the peptide is too short, the antigenicity may be lost. When the peptide is too long, chimeric hepatitis B virus core antigen polypeptides do not easily form a core particle due to self-assembly, as a result of which production of an antibody that specifically recognizes the peptide may not be induced effectively.

When a partial peptide of an autoantigen protein is used as an antigenic peptide in the present invention, the partial peptide is preferably specific to the autoantigen protein. Being "specific" means that a gene product other than the autoantigen protein (excluding variable regions of immunoglobulin and T cell receptor), which is naturally expressed in a mammal from which the autoantigen protein is derived, does not contain the partial peptide.

When a partial peptide of an autoantigen protein is used as an antigenic peptide in the present invention, as the partial peptide to be used, one at a position where the activity of the autoantigen protein is inhibited when an antibody that recognizes the partial peptide binds to the partial peptide in the autoantigen protein, is preferably selected. Such partial peptide can be in a functional site, for example, receptor binding site, divalent ion binding site, site recognized by a specific enzyme and the like. A partial peptide contained in a site removed during the maturation process of protein such as signal sequence and the like, is preferably excluded from partial peptide to be used in the present invention. Those of ordinary skill in the art can select appropriate partial peptide based on the steric structures and the like of autoantigen protein.

When a partial peptide of an autoantigen protein is used as an antigenic peptide in the present invention, specific examples of the partial peptide include the following.
(VEGF) (WO 2014/034735 A1)

a)
IMRIKPHQSQHIG (SEQ ID NO: 1)

b)
MRIKPHQ (SEQ ID NO: 2)

c)
MQIMRIKPHQSQHIGEM (SEQ ID NO: 3)

d) peptide consisting of a partial sequence of amino acid sequence shown in SEQ ID NO: 3, which contains the amino acid sequence shown in SEQ ID NO: 1 or 2 e)
IMRIKPHQGQHIG (SEQ ID NO: 4)

f)
MRIKPHQ (SEQ ID NO: 5)

g)
MQIMRIKPHQGQHIGEM (SEQ ID NO: 6)

h) a peptide consisting of a partial sequence of the amino acid sequence shown in SEQ ID NO: 6, which contains the amino acid sequence shown in SEQ ID NO: 4 or 5

SEQ ID NOs: 1, 2 and 3 are partial amino acid sequences of mouse VEGF-A. SEQ ID NOs: 4, 5 and 6 are partial amino acid sequences of human VEGF-A.

The length of the partial sequence in the above-mentioned (d) and (h) is 8, 9, 10, 11, 12, 13, 14, 15 or 16 amino acids.
(angiopoietin-2) (WO 2014/034735 A1)

a)
PQRQNTNKFNGIKWYY (SEQ ID NO: 7)

b)
YYPQRQNTNKE (SEQ ID NO: 8)

SEQ ID NOs: 7 and 8 are partial amino acid sequences of human angiopoietin-2.
(angiotensin II) (WO 2003/031466 and Journal of Hypertension, vol.25, no.1, pp. 63-72, 2007)

a)
CGGDRVYIHPF (SEQ ID NO: 9)

b)
CGGDRVYIHPFHL (SEQ ID NO: 10)

c)
DRVYIHPFHLGGC (SEQ ID NO: 11)

d)
CDRVYIHPFHL (SEQ ID NO: 12)

e)
CHPFHL (SEQ ID NO: 13)

f)
CGPFHL (SEQ ID NO: 14)

g)
CYIHPF (SEQ ID NO: 15)

h)
CGIHPF (SEQ ID NO: 16)

i)
CGGHPF (SEQ ID NO: 17)

j)
CRVYIGGC (SEQ ID NO: 18)

k)
DRVYGGC (SEQ ID NO: 19)

l)
DRVGGC (SEQ ID NO: 20)

m)
DRVYIHPF (SEQ ID NO: 21)

a)-l) are peptides containing a partial amino acid sequence of angiotensin II. m) is a full-length peptide of angiotensin II. Preferably, DRVYIHPF (SEQ ID NO: 21) is used as an antigenic peptide. When the peptide is used, an antibody having higher specificity to angiotensin II than angiotensin I is induced. Since the amino acid sequence of angiotensin II is common to human, dog, cat, mouse, and rat, each peptide of a)-m) is applicable to not only human but also dog, cat, mouse, and rat.

(cholesteryl ester transfer protein (CETP)) (Vaccine, vol.24, pp. 4942-4950, 2006)

a)
RDGFLLLQMDFGFPEHLLVDFLQSL (SEQ ID NO: 22)

a) is a partial peptide of human, mouse or rabbit CETP.
(apolipoprotein (a))

a)
EAPSEQAPTEQR (SEQ ID NO: 23)

SEQ ID NO: 23 is a partial amino acid sequence of human apolipoprotein (a).
(DPP4) (Proc Natl Acad Sci USA. 2014 Apr. 1; 111(13): E1256-63)

a)
SKDEAAADSRRT (SEQ ID NO: 33)

b)
KSTFRVKSYS (SEQ ID NO: 34)

c)
ENSTFESFG (SEQ ID NO: 35)

a)-c) are partial peptides of mouse DPP4 (a:29-40aa, b:48-57aa, c:89-97aa).
(IL-17) (Immunotherapy, vol. 4, no. 12, 1799-1807, 2012)

a)
SSACPNTEAKD (SEQ ID NO: 36)

b)
KVSSRRPSDYLNRSTS (SEQ ID NO: 37)

c)
HRNEDPDRYPSVIWE (SEQ ID NO: 38)

d)
KREPESCPFT (SEQ ID NO: 39)

e)
EKMLVGVGCTCVASI (SEQ ID NO: 40)

a)-e) are partial peptides of mouse IL-17.

Partial peptides of human ortholog proteins corresponding to the aforementioned partial peptides of non-human mammal proteins may also be useful as an antigenic peptide. Those of ordinary skill in the art can easily identify such antigenic peptide by aligning the amino acid sequence of a protein of a non-human mammal with the amino acid sequence of a human ortholog protein, and specifying a region in the amino acid sequence of the human ortholog protein, which corresponds to the partial peptide to be noted.

In the preparation of the present invention, the antigenic peptide of (I) is preferably isolated. The "isolation" means that an operation to remove factors other than the target cell or component has been performed, and the native state no longer exists. The purity of the "isolated antigenic peptide X" (percentage (weight/weight) of antigenic peptide X in the total peptide amount) is generally not less than 70%, preferably not less than 80%, more preferably not less than 90%, still more preferably not less than 99%, most preferably 100%.

In the preparation of the present invention, the antigenic peptide of (I) may form a complex by being crosslinked to a carrier protein such as bovine serum albumin, KLH (Keyhole Limpet Hemocyanin), VLP (Virus like particle) and the like, to be more easily recognized by the immune system, and contained in the preparation of the present invention. In this case, the purity of the "isolated antigenic peptide X" is calculated as the purity of the isolated complex.

A method of crosslinking the antigenic peptide to a carrier protein is not particularly limited, and a well-known protein crosslinking agent may be used therefor. Examples of the protein crosslinking agent include, but are not limited to, aldehyde (e.g., glutaraldehyde, para-formaldehyde, formaldehyde etc.), hetero divalent reactive crosslinker (ANB-NOS, BMPS, EMCS, GMBS, LC-SPDP, MBS, PDPH, SBA, SIA, SMCC, SMPB, SMPH, SPDP, Sulfo-LC-SPDP, Sulfo-MBS, Sulfo-SANPAH, Sulfo-SMCC etc.), homo divalent reactive crosslinker (BS2G, BS3, DSG, DSP, DSS, DSSeb, DST, DTSSP, EGS, Sulfo-EGS etc.), crosslinker with spacer arm with zero length (CDI, DCC, EDC-HCL, NHS, Sulfo-NHS etc.), deuteration crosslinker (BS2G-d4, BS3-d4, ESG-d4, DSP-d8, DSS-d4 etc.) and the like. A preferable protein crosslinking agent is aldehyde (glutaraldehyde etc.).

When the antigenic peptide does not contain a cysteine residue, a sulfhydryl group may be introduced to facilitate crosslinking, by adding cysteine to the terminal of the antigenic peptide.

In addition, to stably present an antigenic peptide on the complex while maintaining its structure, and facilitate access of an antibody to the antigenic peptide, a spacer sequence may be introduced into the terminal of the antigenic peptide. While the length of the spacer sequence is not limited as long as the antigenicity of the antigenic peptide is not impaired, it is generally 1-10 amino acids, preferably 1-5 amino acids, more preferably 1-3 amino acids.

In one embodiment, the antigenic peptide and the carrier protein (KLH etc.) are fixed with aldehyde (glutaraldehyde etc.), without adding a spacer sequence to the terminal of the antigenic peptide.

Hepatitis B virus core antigen polypeptide used in the present invention is
(1) a polypeptide containing the amino acid sequence shown by SEQ ID NO: 24, or
(2) a polypeptide containing an amino acid sequence having not less than 90% (preferably not less than 95%, more preferably not less than 97%, still more preferably not less than 99%) identity with the amino acid sequence shown by SEQ ID NO: 24, and having an activity to form a core particle due to self-assembly.

Self-assembly refers to a phenomenon wherein molecules dissolved in a solution associate to form an assembly. Core particle refers to a rigid structure having a specific repetitive constitution. In the present specification, the core particle may be a product of synthesis steps or a product of biological steps.

As the polypeptide of the embodiment of (2), a polypeptide containing the amino acid sequence shown by SEQ ID NO: 25 disclosed in WO 2003/031466 can be mentioned. A polypeptide containing the amino acid sequence shown by SEQ ID NO: 25 except that one or plural cysteine residues at the positions 48, 61, 107 and 185 are deleted or substituted by other amino acid residue (e.g., serine residue) is also preferable as the polypeptide of the embodiment of (2). As recognized by those of ordinary skill in the art, in a polypeptide having an amino acid sequence different from that of SEQ ID NO: 25, cysteine residues at similar positions can be deleted or substituted by other amino acid residues, and polypeptides obtained by such deletion or substitution are also encompassed in the polypeptide of the embodiment of (2).

The polypeptide of the embodiment of (2) also encompasses a variant polypeptide wherein the isoleucine residue at the position corresponding to the position 97 of SEQ ID NO: 25 is substituted by leucine residue or phenylalanine residue (Yuan et al., J. Virol. vol. 73, pages 10122-10128 (1999)). In addition, amino acid sequences of many HBcAg variants and several kinds of hepatitis B core antigen precursor variants are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999 and M95589 (each of the disclosures is incorporated in the present specification by reference), and polypeptides containing amino acid sequences of these variants are also encompassed in the polypeptide of the embodiment of (2). The above-mentioned variants have amino acid sequences different at many positions including amino acid residues corresponding to the amino acid residues present at the positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO: 25.

Furthermore, polypeptides containing the amino acid sequences of the HBcAg variants described in WO 01/98333, WO 01/77158 and WO 02/14478, all of which are incorporated in the present specification by reference are also encompassed in the polypeptide of the embodiment of (2).

In Pumpens et al. Intervirology 2001; 44:98-114, the kind of substitutable amino acid in each amino acid residue in hepatitis B virus core antigen polypeptide is described. Based on the information, those of ordinary skill in the art can easily design the polypeptide of the embodiment of (2) by substituting one or multiple amino acids in the amino acid sequence shown in SEQ ID NO: 24 to other amino acid(s).

In the present specification, unless particularly indicated, the positions of amino acid residues in the amino acid sequence of hepatitis B virus core antigen polypeptide are specified with the amino acid sequence shown by SEQ ID NO: 24 as the standard. When a polypeptide does not contain the amino acid sequence shown by SEQ ID NO: 24, the amino acid sequence of the polypeptide is aligned with the amino acid sequence shown by SEQ ID NO: 24, and the position of the corresponding amino acid residue is adopted.

The hepatitis B virus core antigen polypeptide used in the present invention is preferably a polypeptide containing the amino acid sequence shown by SEQ ID NO: 24.

In the preparation of the present invention, in the chimeric hepatitis B virus core antigen polypeptide encoded by the expression vector of (II), the antigenic peptide is inserted in the region of amino acid residues 74-87 or 130-138 in the hepatitis B virus core antigen polypeptide, or added to the N-terminal or C-terminal of the hepatitis B virus core antigen polypeptide. Since the region of amino acid residues 74-87 or 130-138 in the hepatitis B virus core antigen polypeptide is a B cell epitope of the hepatitis B virus core antigen polypeptide (Pumpens et al. Intervirology 2001; 44:98-114), insertion of the antigenic peptide in this region is expected to efficiently induce production of an antibody against the antigenic peptide. Preferably, in chimeric hepatitis B virus core antigen polypeptide, the antigenic peptide is inserted between the amino acid residues 80 and 81 of the hepatitis B virus core antigen polypeptide.

In an embodiment of chimeric hepatitis B virus core antigen polypeptide wherein the antigenic peptide is inserted in the region of amino acid residues 74-87 or 130-138 of the hepatitis B virus core antigen polypeptide, the chimeric hepatitis B virus core antigen polypeptide to be used in the present invention contains the following elements (a)-(c):
(a) N-terminus part polypeptide residues of hepatitis B virus core antigen polypeptide (consisting of the continuous partial amino acid sequence of hepatitis B virus core antigen polypeptide from N-terminus to the amino acid residue x) (wherein X is any integer selected from the group consisting of 74-86 and 130-137, preferably 80),
(b) an antigenic peptide residue, and
(c) C-terminus partial polypeptide residues of hepatitis B virus core antigen polypeptide (consisting of the continuous partial amino acid sequence of hepatitis B virus core antigen polypeptide from the amino acid residue Y to C-terminus) (wherein Y is an integer of X plus 1, preferably 81)
in the order of (a), (b), (c) from the N terminus side.

The chimeric hepatitis B virus core antigen polypeptide to be used in the present invention having the above-mentioned constitution forms a core particle due to self-assembly, and the antigenic peptide residue is presented on the outside of the particle.

The amino acid sequence inserted between constituent element (a) and constituent element (c) may further contain, in addition to constituent element (b) (antigenic peptide residue), one or more (preferably 1-3, more preferably 1) other antigenic peptide residues. A further antigenic peptide residue may be inserted at any position between constituent element (a) and constituent element (b), or constituent element (b) and constituent element (c). The length of the further antigenic peptide residue is generally 5-30 amino acids, preferably 6-25 amino acids, more preferably 10-18 amino acids, furthermore preferably 11-16 amino acids.

When plural antigenic peptide residues are inserted between constituent element (a) and constituent element (c), the antigenic peptide residues may be directly linked by a covalent bond, or linked via a spacer sequence. The spacer sequence means an amino acid sequence containing one or more amino acid residues to be inserted between two adjacent constituent elements contained in the chimeric hepatitis B virus core antigen polypeptide. The antigenic peptide residues are preferably linked via a spacer sequence so that plural antigenic peptide residues can be stably presented while maintaining their structures. The length of the spacer sequence is not limited as long as the chimeric hepatitis B virus core antigen polypeptide forms a core particle by self-assembly, and all inserted antigenic peptide residues are presented outside the particle, and is generally 1-10 amino acids, preferably 1-5 amino acids, more preferably 1-3 amino acids, most preferably 2 or 3 amino acids.

An antigenic peptide residue on the most N-terminus side between constituent element (a) and constituent element (c), and constituent element (a) may be directly linked by a covalent bond or via a spacer sequence. The element (a) and the antigenic peptide residue on the most N-terminus side are preferably linked via a spacer sequence so that the antigenic peptide will be stably presented on the outside of the particle formed by self-assembly of chimeric hepatitis B virus core antigen polypeptides, while maintaining its structure. While the length of the spacer sequence is not limited as long as chimeric hepatitis B virus core antigen polypeptide forms a core particle due to self-assembly and the antigenic peptide is presented on the outside of the particle, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms a core particle due to self-assembly and the antigenic peptide is presented on the outside of the particle. Examples of a preferable spacer sequence include, but are not limited to, IT, GAT, CGG and the like.

An antigenic peptide residue on the most C-terminus between constituent element (a) and constituent element (c), and constituent element (c) may be directly linked by a covalent bond or via a spacer sequence. The antigenic peptide residue on the most C-terminus side and the element (c) are preferably linked via a spacer sequence so that the antigenic peptide will be stably presented on the outside of the particle formed by self-assembly of chimeric hepatitis B virus core antigen polypeptides, while maintaining its structure. While the length of the spacer sequence is not limited as long as chimeric hepatitis B virus core antigen polypeptide forms a core particle due to self-assembly and a antigenic peptide is presented on the outside of the particle, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms a core particle due to self-assembly and a antigenic peptide is presented on the outside of the particle. Examples of a preferable spacer sequence include, but are not limited to, IT, GAT, CGG and the like.

The length of the amino acid sequence inserted between constituent element (a) and constituent element (c) is not particularly limited as long as chimeric hepatitis B virus core antigen polypeptide forms a core particle due to self-assembly, an antigenic peptide is presented on the outside of the particle, and specific immune response to the antigenic peptide can be induced, and is generally 5-80 amino acids. When the inserted amino acid sequence is too short, the antigenicity as an epitope may be lost. When the inserted amino acid sequence is too long, formation of core particle by chimeric hepatitis B virus core antigen polypeptide due to self-assembly becomes difficult, as a result of which an antibody specifically recognizing the antigenic peptide may not be produced.

In an embodiment wherein the target antigenic peptide is added to the N-terminal or C-terminal of the hepatitis B virus core antigen polypeptide, the antigenic peptide and the hepatitis B virus core antigen polypeptide may be directly linked by a covalent bond or via a spacer sequence. The antigenic peptide and hepatitis B virus core antigen polypeptide are preferably linked via a spacer sequence so that the antigenic peptide will be stably presented on the outside of the core particle formed by self-assembly of chimeric hepatitis B virus core antigen polypeptides, while maintaining its structure. The length of the spacer sequence is not limited as long as the chimeric hepatitis B virus core antigen polypeptide forms a core particle by self-assembly, and antigenic peptide is presented outside the particle, and is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms a core particle due to self-assembly and antigenic peptide is presented on the outside of the particle.

In the preparation of the present invention, the expression vector of (II) is a recombinant vector incorporating a polynucleotide encoding the above-mentioned chimeric hepatitis B virus core antigen polypeptide. When the expression vector is administered to a target mammal, the expression vector is incorporated into a cell of the target mammal, and the cell expresses the above-mentioned chimeric hepatitis B virus core antigen polypeptide. Examples of the expression vector inserted with polynucleotide encoding chimeric hepatitis B virus core antigen polypeptide include plasmid, virus, phage, cosmid and other vectors conventionally used in the art. Examples of the plasmid vector include, but are not limited to, pCAGGS (Gene 108: 193-199 (1991)), pCR-X8 (Vaccine 24: 4942-4950 (2006)), pcDNA3.1 (trade name, Invitrogen), pZeoSV (trade name, Invitrogen), pBK-CMV (trade name, Stratagene), pVAX1 (trade name, Life Technologies) and the like. The virus vector is a DNA virus or an RNA virus. Examples of the virus vector include, but are not limited to, detoxicated retrovirus, adenovirus, adeno-associated virus, herpes virus, vaccinia virus, poxvirus, polio virus, Sindbis virus, Hemagglutinating Virus of Japan (HVJ), SV40, human immunodeficient virus (HIV) and the like. Furthermore, Hemagglutinating Virus of Japan envelope (HVJ-E) and the like can also be utilized.

In the above-mentioned expression vector, polynucleotide (preferably DNA) encoding chimeric hepatitis B virus core antigen polypeptide is operably linked to a promoter capable of exhibiting a promoter activity in the cell of a mammal (preferably human, dog, or cat) to be the administration subject.

The promoter to be used is not particularly limited as long as it can function in the cell of a mammal to be the administration subject. Examples of the promoter include pol I promoter, pol II promoter, pol III promoter and the like. Specifically, virus promoters such as SV40-derived initial promoter, cytomegalovirus LTR and the like, mammal constitutive protein gene promoters such as β-actin gene promoter and the like, RNA promoters such as tRNA promoter and the like, and the like are used.

The above-mentioned expression vector preferably contains a transcription termination signal, i.e., terminator region, at the downstream of the polynucleotide encoding chimeric hepatitis B virus core antigen polypeptide. It can further contain a selection marker gene for the selection of a transformed cell (gene conferring resistance to drugs such as tetracycline, ampicillin, kanamycin and the like, gene complementing auxotrophic mutation etc.).

In one embodiment, the above-mentioned expression vector may contain an immune stimulatory sequence (ISS) (also referred to as CpG) to potentiate the immune effect. The immune stimulatory sequence is a DNA containing a non-methylated CpG motif of bacterium, and is known to function as a ligand of a particular receptor (Toll-like receptor 9) (see Biochim. Biophys. Acta 1489, 107-116 (1999) and Curr. Opin. Microbiol. 6, 472-477 (2003) for the detail). Preferable examples of the immune stimulatory sequence include the following.

```
CpG-B1018 22 bp
                                        (SEQ ID NO: 26)
5'-tga ctg tga acg ttc gag atg a-3'

CpG-A D19 20bp (D type)
                                        (SEQ ID NO: 27)
5'-ggt gca tcg atg cag ggg gg-3'

CpG-CC274 21 bp
                                        (SEQ ID NO: 28)
5'-tcg tcg aac gtt cga gat gat-3'

CpG-CC695 25 bp
                                        (SEQ ID NO: 29)
5'-tcg aac gtt cga acg ttc gaa cgt t-3'
```

Alternatively, 2, 3 or 4 from these ISSs may be ligated and used. Preferable examples of the ligated ISS sequence include the following.

5'-ggt gca tcg atg cag ggg gg tga ctg tga acg ttc gag atg a tcg tcg aac gtt cgagat gat tcg aac gtt cga acg ttc gaa cgt t-3' (SEQ ID NO: 30)

Those of ordinary skill in the art can construct the aforementioned expression vector according to well-known genetic engineering techniques described in, for example, "edit. Sambrook et al., Molecular Cloning A Laboratory Manual Cold Spring Harbor Laboratory (1989) N.Y.", "edit. Ausubel et al., Current Protocols in Molecular Biology (1987) John Wiley & Sons" and the like.

The preparation of the present invention may be a single preparation obtained by simultaneously formulating the antigenic peptide of (I) and the expression vector of (II), or may be a combination of two kinds of preparations obtained by separately formulating the antigenic peptide of (I) and the expression vector of (II). In a preferable embodiment, the preparation of the present invention is a single preparation obtained by simultaneously formulating the antigenic peptide of (I) and the expression vector of (II).

The preparation of the present invention can be provided as a pharmaceutical composition containing, in addition to an effective amount of the antigenic peptide of (I) and/or the expression vector of (II), any carrier, for example, a pharmaceutically acceptable carrier.

Examples of the pharmaceutically acceptable carrier include, though not limited thereto, excipients such as sucrose, starch, mannit, sorbit, lactose, glucose, cellulose, talc, calcium phosphate, calcium carbonate and the like, binders such as cellulose, methylcellulose, hydroxypropylcellulose, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyrrhizin-ammonium salt, glycine, orange powder and the like, preservatives such as sodium benzoate, sodium bisulfite, methylparaben, propylparaben and the like, stabilizers such as citric acid, sodium citrate, acetic acid and the like, suspending agent such as methylcellulose, polyvinylpyrrolidone, aluminum stearate and the like, dispersing agents such as surfactant and the like, diluents such as water, saline and the like, base waxes such as cacao butter, polyethylene glycol, white kerosine and the like, and the like.

While the preparation of the present invention can be administered orally or parenterally to a subject mammal, the preparation of the present invention is preferably administered parenterally to a mammal.

A preparation preferable for parenteral administration (e.g., subcutaneous injection, intradermal injection, intramuscular injection, local injection, intraperitoneal administration and the like) is an aqueous or nonaqueous isotonic aseptic injection liquid, which may contain an antioxidant, a buffer, a bacteriostatic agent, an isotonicity agent and the like. In addition, an aqueous or nonaqueous aseptic suspension can be mentioned, which may contain a suspending agent, a solubilizer, a thickener, a stabilizer, a preservative and the like. Such preparation can be sealed in a container such as ampoule, vial, syringe cartridge, by unit dosage or multiple doses. Also, it is possible to freeze-dry the active ingredient and a pharmaceutically acceptable carrier, and preserve them in a form that requires dissolving or suspending in an appropriate sterile vehicle immediately before use. In one embodiment, the preparation of the present invention is provided as a preparation in which effective amounts of the antigenic peptide of (I) and the expression vector of (II), and a pharmaceutically acceptable carrier are sealed in a container by unit dosage or multiple doses. In another embodiment, the preparation of the present invention is provided as a combination of a preparation in which an effective amount of the antigenic peptide of (I) and a pharmaceutically acceptable carrier are sealed in a container by unit dosage or multiple doses and a preparation in which an effective amount of the expression vector of (II) and a pharmaceutically acceptable carrier are sealed in a container by unit dosage or multiple doses.

The preparation of the present invention may further contain an adjuvant to potentiate a specific immune response to the antigenic peptide. Examples of the adjuvant include aluminum hydroxide, complete Freund's adjuvant, incomplete Freund's adjuvant, pertussis adjuvant, poly(I:C), CpG-DNA and the like. When the expression vector of (II) contains an immunostimulatory sequence (ISS), ISS is not encompassed in the adjuvant here.

In the preparation of the present invention, an induction effect of a specific immune response to the antigenic peptide is enhanced by combining the antigenic peptide of (I) and the expression vector of (II). Therefore, a specific immune response to the antigenic peptide can be sufficiently induced without requiring the aforementioned adjuvant. In one embodiment, therefore, the preparation of the present invention does not contain an adjuvant. In this embodiment, to increase uptake of the antigenic peptide of (I) and the expression vector of (II) into antigen presenting cells, promote presentation of antigenic peptide by antigen presenting cells, and strongly induce specific immune response to the antigenic peptide, the preparation of the present invention is preferably administered (injected) intradermally, subcutaneously, or intramuscularly.

To promote introduction of the expression vector of (II) into cells, the preparation of the present invention may further contain a reagent for nucleic acid introduction. As the reagent for nucleic acid introduction, cationic lipids such as lipofectin (trade name, Invitrogen), lipofectamine (trade name, Invitrogen), transfectam (trade name, Promega), DOTAP (trade name, Roche Applied Science), dioctadecylamidoglycyl spermine (DOGS), L-dioleoyl phosphatidylethanolamine (DOPE), dimethyldioctadecyl-ammonium bromide (DDAB), N,N-di-n-hexadecyl-N,N-dihydroxyethylammonium bromide (DHDEAB), N-n-hexadecyl-N,N-dihydroxyethylammonium bromide (HDEAB), polybrene, poly(ethyleneimine) (PEI) and the like can be used. In addition, the expression vector of (II) may be included in any known liposome constituted of a lipid bilayer such as electrostatic liposome. Such liposome may be fused with a virus such as inactivated Hemagglutinating Virus of Japan (HVJ). HVJ-liposome has a very high fusion activity with a cellular membrane, as compared to general liposomes. When retrovirus is used as an expression vector, RetroNectin, fibronectin, polybrene and the like can be used as transfection reagents.

In the preparation of the present invention, an induction effect of a specific immune response to the antigenic peptide is enhanced by combining the antigenic peptide of (I) and the expression vector of (II). Therefore, a sufficient, specific immune response to the antigenic peptide can be induced without requiring the aforementioned reagent for nucleic acid introduction. In one embodiment, therefore, the preparation of the present invention does not contain a reagent for nucleic acid introduction. In this embodiment, to increase uptake of the antigenic peptide of (I) and the expression vector of (II) into antigen presenting cells, promote presentation of antigenic peptide by antigen presenting cells, and strongly induce specific immune response to the antigenic peptide, the preparation of the present invention is preferably administered (injected) intradermally, subcutaneously, or intramuscularly.

While the content of the antigenic peptide of (I) in the pharmaceutical composition is not particularly limited and is appropriately selected from a wide range, it is generally about 0.00001 to 99 wt % of the whole pharmaceutical composition. While the content of the expression vector of (II) in the pharmaceutical composition is not particularly limited and is appropriately selected from a wide range, it is generally about 0.00001 to 99 wt % of the whole pharmaceutical composition. The above-mentioned numerical value ranges are applicable whether the preparation of the present invention is a single preparation obtained by simultaneously formulating the antigenic peptide of (I) and the expression vector of (II), or a combination of two kinds of preparations obtained by separately formulating the antigenic peptide of (I) and the expression vector of (II).

In the preparation of the present invention, the antigenic peptide of (I) and the expression vector of (II) are substantially simultaneously administered to a subject.

Being "substantially simultaneous" means that one of the antigenic peptide of (I) and the expression vector of (II) is administered and the other is additionally administered before the antigenic peptide-specific acquired immune response is induced by the earlier administration. In the substantially simultaneous administration of the antigenic peptide of (I) and the expression vector of (II), the time interval between the administration of the antigenic peptide of (I) and that of the expression vector of (II) is generally within 24 hr, preferably within 12 hr, within 6 hr, within 2 hr, within 1 hr, within 30 min, within 15 min, within 5 min, or within 1 min, most preferably 0 min (simultaneous). The "boost" for potentiating an immune response reaction by administering one of the antigenic peptide of (I) and the expression vector of (II) and additionally administering the other after the antigenic peptide-specific acquired immune response is induced by the earlier administration is not included in the "substantially simultaneous" administration.

The administration form of the antigenic peptide of (I) and the expression vector of (II) is not particularly limited as long as the antigenic peptide of (I) and the expression vector of (II) are substantially simultaneously administered to a subject. Examples of such administration form include (1) administration of a single preparation obtained by simultaneously formulating the antigenic peptide of (I) and the expression vector of (II), (2) simultaneous administration of two kinds of preparations of the antigenic peptide of (I) and the expression vector of (II), which have been separately formulated, by the same administration route,
(3) administration of two kinds of preparations of the antigenic peptide of (I) and the expression vector of (II), which have been separately formulated, by the same administration route in a staggered manner,
(4) simultaneous administration of two kinds of preparations of the antigenic peptide of (I) and the expression vector of (II), which have been separately formulated, by different administration routes,
(5) administration of two kinds of preparations of the antigenic peptide of (I) and the expression vector of (II), which have been separately formulated, by different administration routes in a staggered manner (e.g., administration in the order of the expression vector of (II) and the antigenic peptide of (I), or in the reverse order) and the like.

In a preferable embodiment, a single preparation obtained by simultaneously formulating the antigenic peptide of (I) and the expression vector of (II) is administered to a subject.

The preparation of the present invention may be administered by any method as long as a specific immune response to an antigenic peptide is induced in a mammal to be the administration subject. Preferably, the preparation of the present invention is parenterally administered in an amount sufficient for inducing a specific immune response to an antigenic peptide in a subject. Examples of the administration method include intradermal, subcutaneous, intramuscular, intravenous, intraperitoneal or intraadipose tissue administration, or administration via a pathway in mammalian gland tissue; gas-induced particle bombardment method (by electron gun and the like); administration with a needleless syringe (including spring type (e.g., ShimaJET® etc.), powder type (e.g., Daicel etc.)); a method via a mucosal pathway in the form of collunarium and the like, and the like. To increase uptake of the antigenic peptide of (I) and the expression vector of (II) into antigen presenting cells, promote presentation of antigenic peptide by antigen presenting cells, and strongly induce specific immune response to the antigenic peptide, the preparation of the present invention is preferably administered (injected) intradermally, subcutaneously, or intramuscularly.

When the antigenic peptide of (I) and the expression vector of (II) are administered separately, respective administration methods may be the same or different. Preferably, they are administered by the same method. In this embodiment, the antigenic peptide of (I) and the expression vector of (II) are preferably administered intradermally, subcutaneously or intramuscularly to a subject. In this case, while the administration sites of the antigenic peptide of (I) and the expression vector of (II) may be the same or different, they are preferably administered at the same site.

In a preferable embodiment, a single preparation obtained by simultaneously formulating the antigenic peptide of (I) and the expression vector of (II) is intradermally, subcutaneously or intramuscularly administered to a subject.

In one embodiment, the preparation of the present invention is intradermally, subcutaneously or intramuscularly administered by a needleless injector. The needleless injector is preferably a pressure syringe. Examples of the needleless injector include, but are not limited to, ShimaJET (trade name, SHIMADZU CORPORATION), Twin-Jector EZ II (trade name, Japan chemical research), Syrijet (trade name, Keystone), ZENEO (trade name, Crossject) and the like. In this case, the preparation of the present invention can be provided as an injection preparation containing the antigenic peptide of (I), the expression vector of (II) and needleless injector, wherein the antigenic peptide of (I) and the expression vector of (II) are enclosed in the needleless injector.

In one embodiment, the preparation of the present invention is administered subcutaneously, intradermally or intramuscularly with a gene gun. In this case, the antigenic peptide of (I) and the expression vector of (II) may be applied onto the carrier particles such as colloidal gold particles and the like to be introduced into a living body and used for administration. A technique for coating carrier particles with polynucleotide is known (see, for example, WO 93/17706).

In the preparation of the present invention, an induction effect of a specific immune response to the antigenic peptide is enhanced by combining the antigenic peptide of (I) and the expression vector of (II). Therefore, a specific immune response to an antigenic peptide can be sufficiently induced by administering to a subject of administration, without requiring a special device or apparatus such as needleless syringe, gene gun and the like as mentioned above. For example, the antigenic peptide of (I) and the expression vector of (II) are intradermally, subcutaneously or intramuscularly administered to a subject with a general syringe (with needle).

The preparation of the present invention may be substantially simultaneously administered to plural sites (e.g., 2-10 sites) of a subject of administration. A good immune response can be obtained by administering the preparation of the present invention to multiple sites.

The number of administrations of the preparation of the present invention is not particularly limited as long as a specific immune response to an antigenic peptide is induced, and the preparation may be administered only once or multiple times. When the preparation of the present invention is divided and substantially simultaneously administered multiple times, multiple times of substantially simultaneous administration are gathered and counted as a single time of administration of the preparation of the present invention. For example, in an embodiment in which the antigenic peptide of (I) and the expression vector of (II) are separately administered substantially simultaneously, a single time administration of the antigenic peptide of (I) and a single time administration of the expression vector of (II) are added and counted as a single time administration of the preparation of the present invention. When the preparation of the present invention is substantially simultaneously administered to multiple sites of a subject of administration, the multiple times of substantially simultaneous administrations are added and counted as a single time administration. In one embodiment, to induce good immune responses, the preparation of the present invention is administered multiple times at given intervals. While the number of administrations can be appropriately determined by monitoring the level of immune response, it is generally 2-10 times, preferably 2-6 times. The frequency of administrations is generally once a week to once a year, preferably once every 1 to 6 months.

In the preparation of the present invention, an induction effect of a specific immune response to the antigenic peptide is enhanced by combining the antigenic peptide of (I) and the expression vector of (II). In one embodiment, therefore, a specific immune response to the antigenic peptide can be sufficiently induced even by a single time administration.

By introducing the expression vector of (II) into a tissue (or cell) of a subject mammal, the preparation of the present invention induces in vivo expression of the above-mentioned chimeric hepatitis B virus core antigen polypeptide, and induces a specific immune response to the antigenic peptide (preferably, production of antibody that specifically recognizes the antigenic peptide) as a result of immunization of the expressed chimeric hepatitis B virus core antigen polypeptide and administered antigenic peptide of (I). Various methods for introducing nucleic acids such as expression vector and the like into a living body are known (T. Friedman, Science 244: 1275-1281 (1989)), and any introduction method can be adopted as long as it can induce in vivo expression of the above-mentioned chimeric hepatitis B virus core antigen polypeptide, and a specific immune response to antigenic peptide (preferably, production of antibody that specifically recognizes the antigenic peptide).

Examples of the method for introducing an expression vector into a mammalian tissue (or cell) in vivo include, but are not limited to, inner liposome method, electrostatic liposome method, HVJ-liposome method, HVJ-AVE liposome method, receptor-mediated gene transfer, particle gun method, naked DNA method, introduction method by positively charged polymer, electroporation method and the like.

In the preparation of the present invention, an induction effect of a specific immune response to the antigenic peptide is enhanced by combining the antigenic peptide of (I) and the expression vector of (II). Therefore, in one embodiment, a specific immune response to the antigenic peptide can also be sufficiently induced by a comparatively mild introduction method such as a naked DNA method. In this embodiment, to increase uptake of the antigenic peptide of (I) and the expression vector of (II) into antigen presenting cells, promote presentation of antigenic peptide by antigen presenting cells, and strongly induce specific immune response to the antigenic peptide, the preparation of the present invention is preferably administered (injected) intradermally, subcutaneously, or intramuscularly.

As for the dose of the preparation of the present invention, effective amounts (amount that induces specific immune response to antigenic peptide) of the antigenic peptide of (I) and the expression vector of (II) are administered. While the dose depends on the administration method, conditions of the administration subject (sex, age, body weight and the like), immunogenicity of antigenic peptide in a mammal to be the administration subject, the strength of the regulatory sequence such as promoter contained in expression vector and the like, those of ordinary skill in the art can determine the dose necessary for a good immune response by administering a given amount of the antigenic peptide of (I) and the expression vector of (II) to a mammal to be the administration subject, measuring the antibody titer specific to the antigenic peptide by a detection method such as ELISA and the like, and observing the immune response. The dose of the antigenic peptide of (I) for subcutaneous, intradermal or intramuscular administration to a mammal (e.g., human, dog, cat) by injection is, for example, 1 μg-1 mg, preferably about 5 μg-50 μg, as the amount of antigenic peptide per single time administration, but the dose is not limited thereto. The dose of the expression vector of (II) for subcutaneous, intradermal or intramuscular administration to a mammal (e.g., human, dog, cat) by injection is, for example, 1 μg-200 μg, preferably about 5 μg-100 μg, as the amount of expression vector per single time administration, but the dose is not limited thereto.

In one embodiment, the preparation of the present invention has an action to "induce synergistic immune response specific to antigenic peptide". As used herein, the "action to induce synergistic immune response specific to antigenic peptide" means "an action to induce immune response specific to antigenic peptide" which exceeds the total of "an action to induce immune response specific to antigenic peptide by single administration of the antigenic peptide of (I)" and "an action to induce immune response specific to antigenic peptide by single administration of the expression vector of (II)". In this embodiment, synergistically effective amounts of the antigenic peptide of (I) and the expression vector of (II) are administered to an application subject.

As mentioned above, the preparation of the present invention, when an autoantigen protein which is an antigen that contributes to the exacerbation of a particular disease (e.g., lifestyle-related disease) or a partial peptide thereof is used is as antigenic peptide, an immune response specific to the autoantigen protein or a partial peptide thereof, preferably, a humoral immune response specific to the peptide (i.e., production of antibody that specifically recognizes the peptide), is induced, and the activity of the autoantigen protein is neutralized by the antibody, whereby the disease exacerbated by the involvement of the autoantigen protein (e.g., lifestyle-related disease) can be prevented or treated. Therefore, the preparation of the present invention can be used as a prophylactic or therapeutic agent for such diseases.

For example, when angiotensin II, angiotensin I, ACE, renin, or a partial peptide thereof is used as an antigenic peptide, the preparation of the present invention can be used as a prophylactic or therapeutic agent for renal failure, cardiac failure, hypertension, hyperlipidemia, arteriosclerosis (arteriosclerosis obliterans etc.), myocardial infarction, cerebral infarction, dementia and the like. When CETP is used as an antigenic peptide, the preparation of the present invention can be used as a prophylactic or therapeutic agent for hyperlipidemia. When VEGF or angiopoietin-2 is used as an antigenic peptide, the preparation of the present invention can be used as a prophylactic or therapeutic agent for cancer (particularly solid tumor), diabetic retinopathy, age-related macular degeneration, retinopathy of prematurity and the like. When apolipoprotein (a) is used as an antigenic peptide, the preparation of the present invention can be used as a prophylactic or therapeutic agent for arteriosclerosis (particularly, atherosclerosis). When PCSK9 or a partial peptide thereof is used as an antigenic peptide, the preparation of the present invention can be used as a prophylactic or therapeutic agent for high LDLemia. When DPP4 or a partial peptide thereof is used as an antigenic peptide, the preparation of the present invention can be used as a prophylactic or therapeutic agent for diabetes and insulin resistance. When IL-17 is used as an antigenic peptide, the preparation of the present invention can be used as a prophylactic or therapeutic agent for autoimmune disease or inflammatory disease such as rheumatism, SLE, ulcerative colitis and the like; and cancer.

Particularly, when angiotensin II or a partial peptide thereof is used as an antigenic peptide, the preparation of the present invention affords a superior effect as a prophylactic or therapeutic agent for cardiac failure in dogs. In many cases of human cardiac failure, left ventricle is thickened and becomes hard by hypertension to cause diastolic dysfunction. Many cases of cardiac failure in dogs occur since the mitral valve is not properly closed due to a valvular disease, as a result of which the delivery of blood becomes bad and the burden on the heart increases. The present inventors have found that the preparation of the present invention is extremely effective for cardiac failure caused by such valvular disease (mitral insufficiency). For example, since a subject (e.g., dog) that developed mitral insufficiency has a high risk of developing cardiac failure, cardiac failure caused by mitral insufficiency can be prevented by administering an effective amount of the preparation of the present invention using angiotensin II or a partial peptide thereof as an antigenic peptide to such subject. Also, by administering an effective amount of the preparation of the present invention using angiotensin II or a partial peptide thereof as an antigenic peptide to a subject (e.g., dog) that developed cardiac failure caused by mitral insufficiency, the cardiac failure can be treated.

In addition, since an increase in the blood pressure of glomerulus and glomerulus hypertrophy due to angiotensin II are considered to be one of the major causes of renal failure (particularly renal failure in cats), the preparation of the present invention using angiotensin II or a partial peptide thereof as an antigenic peptide is expected to be effective.

As described above, when the preparation of the present invention is used for the prophylaxis or treatment of a particular disease, the application subject may be a patient suffering from the disease, a person having a history of having the disease or a person having a risk of developing the disease but not affected with the disease. By administering the agent of the present invention to a patient having the particular disease, a neutralizing antibody against an antigen that contributes to exacerbation of the disease is induced to treat the disease. By administering the agent of the present invention to a person having a history of having the particular disease, a neutralizing antibody against an antigen that contributes to exacerbation of the disease is induced, whereby recurrence of the disease can be suppressed. By administering the agent of the present invention to a person having a risk of developing the disease but not affected with the disease, a neutralizing antibody against an antigen that contributes to exacerbation of the disease is induced, whereby the onset of the disease can be prevented.

As described above, when the preparation of the present invention is used for the prophylaxis or treatment of a particular disease, the preparation of the present invention in an amount effective for the prophylaxis or treatment of the disease (preferably, amount effective for synergistic prophylaxis or treatment) is administered to a subject.

All references cited in the present specification, including publication, patent document and the like, are hereby incorporated in full by reference, to the extent that they have been disclosed herein.

The present invention is explained in more detail in the following by referring to Examples, which do not limit the present invention in any way.

EXAMPLES

Reference Example 1

Increase in Antibody Titer to Angiotensin II by Vaccine Administration
(Method)

A DNA fragment encoding a modified HBc, wherein a spacer sequence and the amino acid sequence DRVYIHPF (SEQ ID NO: 21) of angiotensin II are inserted between the amino acid residues 80 and 81 of HBc, were obtained by PCR and ligation. This DNA fragment was TA-cloned into pcDNA 3.1/V5-His TOPO TA Expression Kit (Invitrogen) to give the pcDNA3.1-HBc-AngII vector.

Six dogs were divided into 3 groups (n=2 per group), immunized with pcDNA3.1-HBc-AngII according to the following 3 protocols, and the antibody titer of the peripheral blood to angiotensin II was measured on day 0, 4 weeks later, and 6 weeks later, with the day of the start of immunization as day 0.

(I) pcDNA3.1-HBc-AngII prepared to 100 µg/100 µl was intradermally administered per single time administration to the dogs at 4 sites by using needleless syringe ShimaJET® (trade name, Shimadzu Corporation). The dose was 0.4 mg/time/dog. This administration was performed twice on day 0 and day 14.

(II) pcDNA3.1-HBc-AngII prepared to 150 µg/100 µl was intradermally administered together with CpG DNA (total dose 160 µg/time/dog) per single time administration to the dogs at 8 sites by using ShimaJET®. The dose of pcDNA3.1-HBc-AngII was 1.2 mg/time/dog. This administration was performed twice on day 0 and day 14. CpG DNA used was a 1:1 mixture of single strand DNAs having the following two sequences.

```
No. 2006:
                                  (SEQ ID NO: 31)
TCGTCGTTTTGTCGTTTTCTCGTT

No. YW07:
                                  (SEQ ID NO: 32)
TCGTCGTTAACGTTAACGCTA
```

(III) pcDNA3.1-HBc-AngII prepared to 3 mg/2 ml was intramuscularly administered together with CpG DNA (total dose 160 µg/time/dog) at one site. The dose of pcDNA3.1-HBc-AngII was 3.0 mg/time/dog. This administration was performed twice on day 0 and day 14.

(Results)

The intramuscular administration of pcDNA3.1-HBc-AngII hardly increased the antibody titer to angiotensin II. At 6 weeks after the administration by ShimaJET®, the antibody titer to angiotensin II increased somewhat.

Example 1

Increase in Antibody Titer by DNA-Peptide Combination Vaccine

Eight dogs were divided into 4 groups (n=2 per group), immunized with pcDNA3.1-HBc-AngII and a conjugate of a partial peptide of angiotensin II and KLH (AngII-KLH) according to the following 4 protocols, and the antibody titer of the peripheral blood to angiotensin II was measured over time.

(I) pcDNA3.1-HBc-AngII prepared to 250 µg/100 µl was intradermally administered together with CpG DNA (total dose 40 µg/time/dog) per single time administration to the dogs at 4 sites by using ShimaJET®. The dose of pcDNA3.1-HBc-AngII was 1.0 mg/time/dog. This administration was performed three times on day 0, day 14 and day 42. (DNA single administration group 1)

(II) AngII-KLH prepared to 12.5 µg/250 µl was intradermally administered together with CpG DNA (total dose 40 µg/time/dog) per single time administration to the dogs at 2 sites. The dose of AngII-KLH was 25 µg/time/dog. This administration was performed three times on day 0, day 14 and day 42. (peptide single administration group)

(III) A solution prepared to a final concentration of pcDNA3.1-HBc-AngII of 250 µg/100 µl, and a final concentration of AngII-KLH of 6.25 µg/100 µl was intradermally administered together with CpG DNA (total dose 40 µg/time/dog) per single time administration to the dogs at 4 sites by using ShimaJET®. The dose of pcDNA3.1-HBc-AngII was 1.0 mg/time/dog, and the dose of AngII-KLH was 25 µg/time/dog. This administration was performed 3 times on day 0, day 14 and day 42. (DNA-peptide combination group)

(IV) pcDNA3.1-HBc-AngII prepared to 250 µg/100 µl was intradermally administered together with CpG DNA (total dose 80 µg/time/dog) per single time administration to the dogs at 8 sites by using ShimaJET®. The dose of pcDNA3.1-HBc-AngII was 2.0 mg/time/dog. This administration was performed 4 times on day 0, day 14, day 28 and day 42. (DNA single administration group 2)
(Results)

The antibody titer to angiotensin II increased in the peptide single administration group (II) and DNA-peptide combination group (III) (FIG. 1). Particularly, the antibody titer increased remarkably in the combination group (III).

Figure 2:
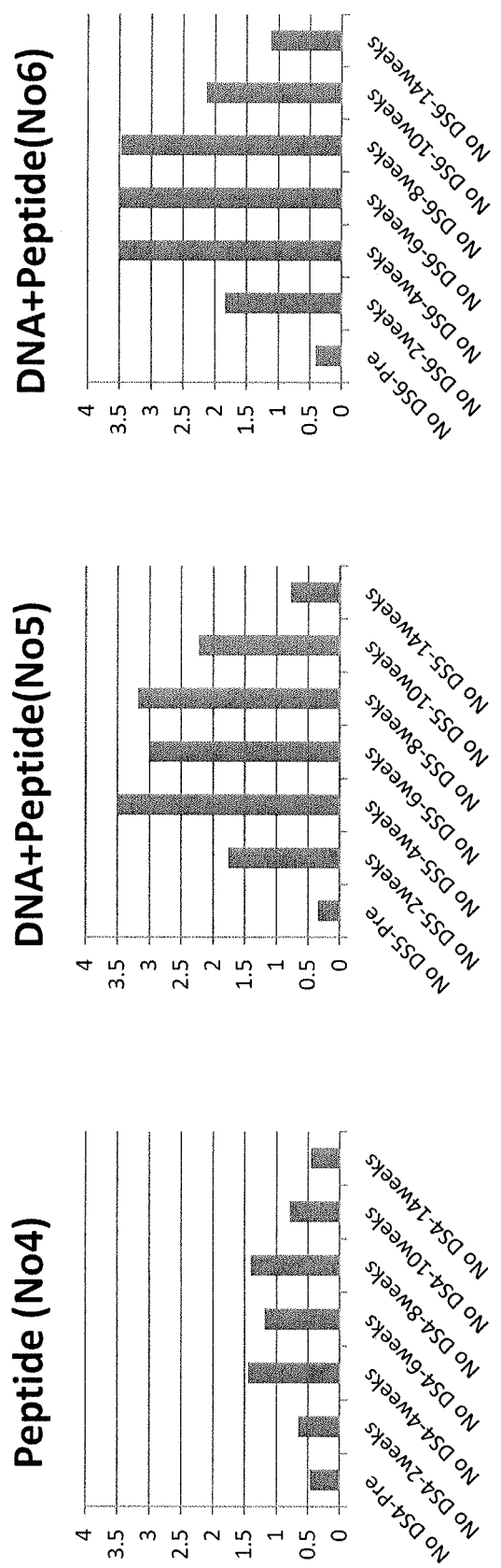
FIG. 2 shows long-term maintenance of an antibody titer to angiotensin II that increased by the administration of a DNA-peptide combination vaccine.

It was confirmed in the DNA-peptide combination group (III) that a high antibody titer to angiotensin II is maintained for about 2 months from 2 to 10 weeks after the start of the administration (FIG. 2).

Figure 3:
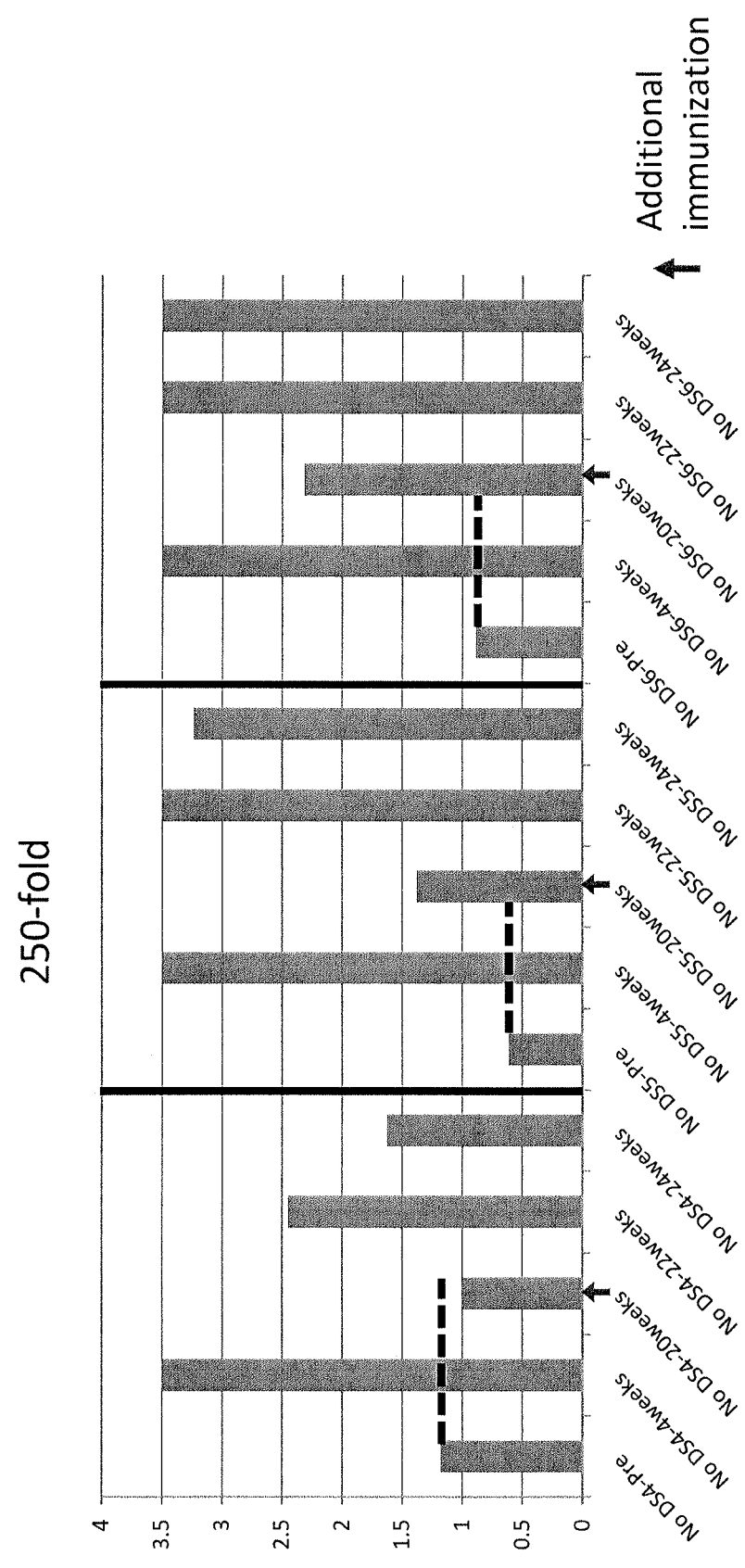
FIG. 3 shows a booster effect by additional immunization on peptide single administration group (No. 4) and DNA-peptide combination vaccine administration group (No. 5, 6).

In the DNA-peptide combination group (III), a significant antibody titer to angiotensin II was confirmed even after 20 weeks from the start of the administration (FIG. 3). When an additional administration was performed at 20 weeks from the start of the administration, a booster effect was found in both the peptide single administration group (II) (No. 4) and DNA-peptide combination group (III) (No. 5, 6), and the effect was stronger in the combination group (III) (FIG. 3).

When observed at a high dilution rate (1250-fold diluted), the antibody titer that increased by the additional immunization on week 20 was lower than the peak after 3 times of administration. The combination group (III) showed a higher booster effect than the peptide single administration group (II).

Figure 4:
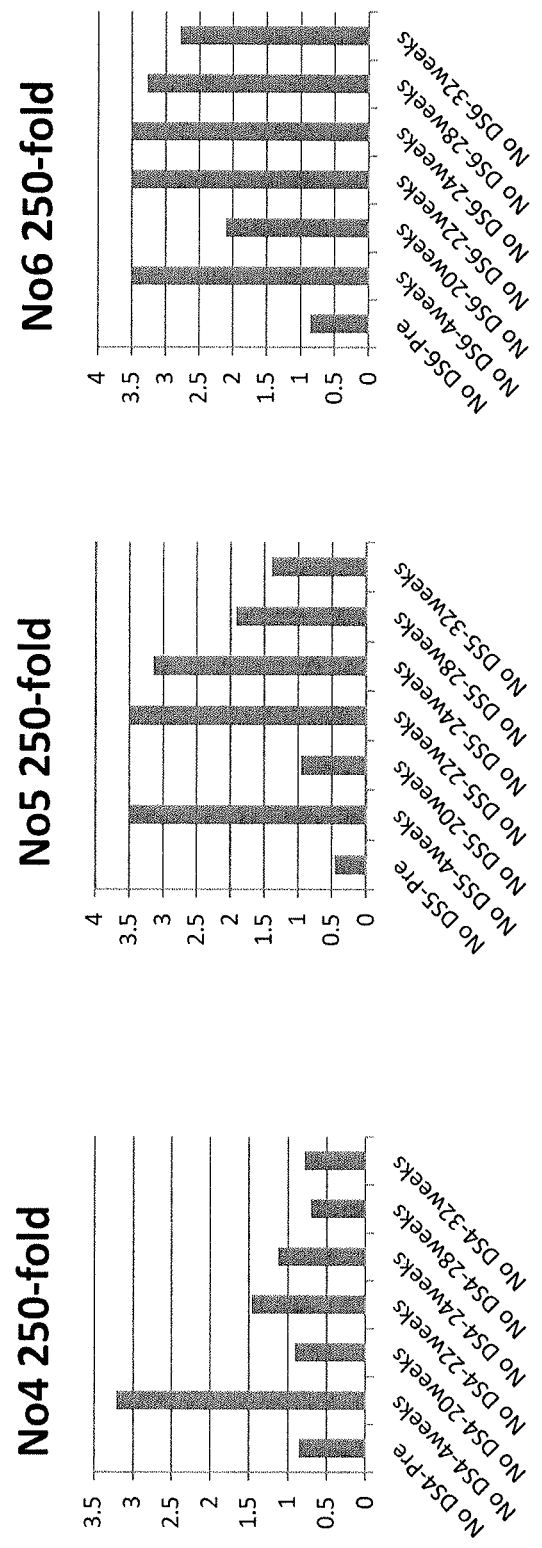
FIG. 4 shows time-course changes in the antibody titer to angiotensin II, after additional immunization of peptide single administration group (No. 4) and DNA-peptide combination vaccine administration group (No. 5, 6).

The increase in the antibody titer by additional immunization was maintained for a longer term in the DNA-peptide combination group (III) (No. 5, 6) than the peptide single administration group (II) (No. 4) (FIG. 4).

Example 2

Effect of DNA-Peptide Combination Vaccine on Cardiac Failure Model Dog
(Method)

The effect of the DNA-peptide combination vaccine was studied according to the following protocol.
dog: n=3
cardiac failure model: Cardiac failure model dog was generated by surgical cutting of mitral valve to cause chordae tendinae mitral insufficiency 4 weeks before the start of vaccine administration.
vaccine: pcDNA3.1-HBc-AngII+AngII-KLH
administration schedule
(I) vaccine administration group
[(pcDNA3.1-HBc-AngII final concentration 250 µg/100 µl+AngII-KLH final concentration 6.25 µg/100 µl)×4 sites (DNA 1 mg+peptide 25 µg)+CpG (dose 40 µg/time/dog)]×3 times (on day 0, day 14, and day 42) (ShimaJET®)
(II) control group
saline×4 sites×3 times (on day 0, day 14, and day 42) (ShimaJET®)
evaluation item Time-course changes of the antibody titer to angiotensin II in the peripheral blood were measured.

As a parameter of cardiac failure, time-course changes of the amount of change of average blood pressure (dMAP), the amount of change of left atrial pressure (dLAP), the amount of change of systemic vessel resistance (dSVR) and the amount of change of cardiac output (dCO) were measured. The blood pressure and LAP were measured by telemetry. CO was measured by echocardiography.
(Results)

Figure 5:
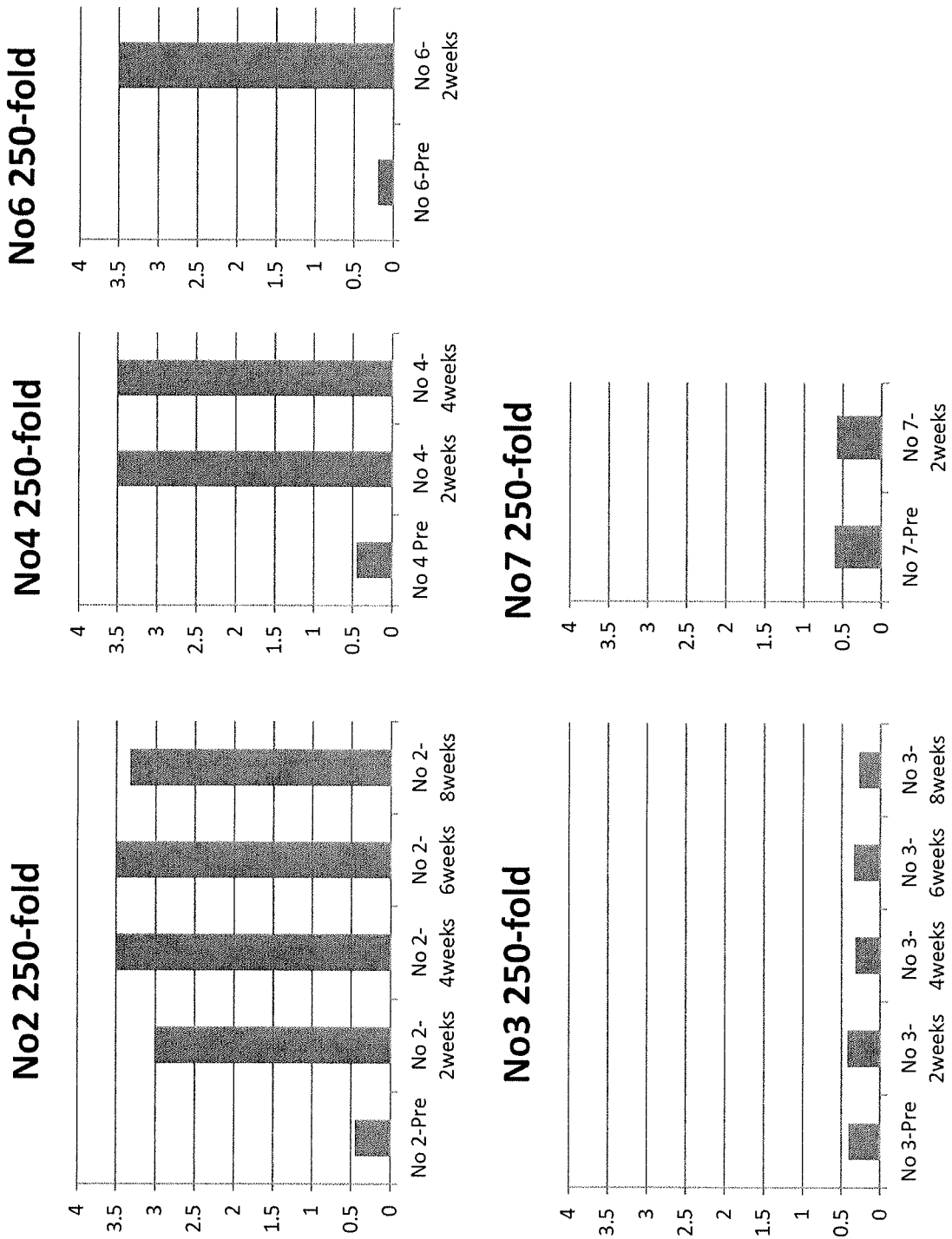
FIG. 5 shows an increase in the antibody titer to angiotensin II by the administration of a DNA-peptide combination vaccine (No. 2, 4, 6).

The vaccine administration groups (Nos. 2, 4, 6) showed a significant increase in the antibody titer to angiotensin II (FIG. 5).

Figure 6:
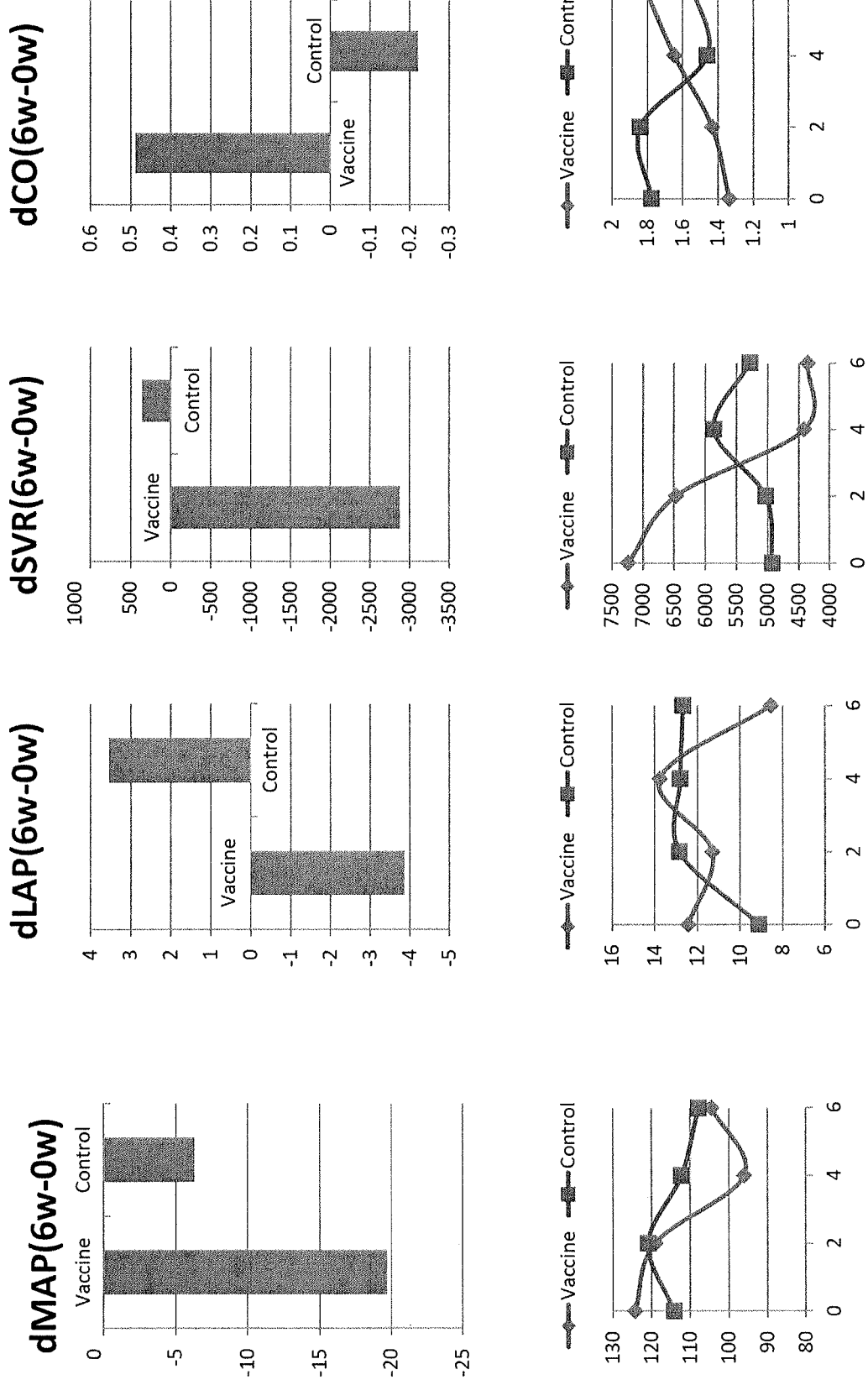
FIG. 6 shows blood pressure lowering effect and cardiac failure parameter improving effect by the administration of a DNA-peptide combination vaccine.

The vaccine administration group showed a tendency of cardiac failure parameter improvement along with a tendency toward a decrease in the blood pressure (FIG. 6).

Example 3

Effect of DNA-Peptide Combination Vaccine on SHR Rat

The effect of the DNA-peptide combination vaccine was studied according to the following protocol.
SHR rat (spontaneously hypertensive rat): n=3
vaccine: pcDNA3.1-HBc-AngII and/or AngII-KLH As a control vector, pcDNA3.1-HBc free of insertion of AngII peptide was used.
test group
(I) pcDNA3.1-HBc-AngII+AngII-KLH (ShimaJET®, intradermal)
(II) pcDNA3.1-HBc+AngII-KLH (ShimaJET®, intradermal)
(III) AngII-KLH (ShimaJET®, intradermal)
(IV) pcDNA3.1-HBc-AngII+AngII-KLH (intramuscular)
(V) Freund's adjuvant+AngII-KLH (subcutaneous)
All administered on day 0, day 14, and day 28.
evaluation item Time-course changes of the antibody titer to angiotensin II in the peripheral blood were measured.
(Results)

Figure 7:
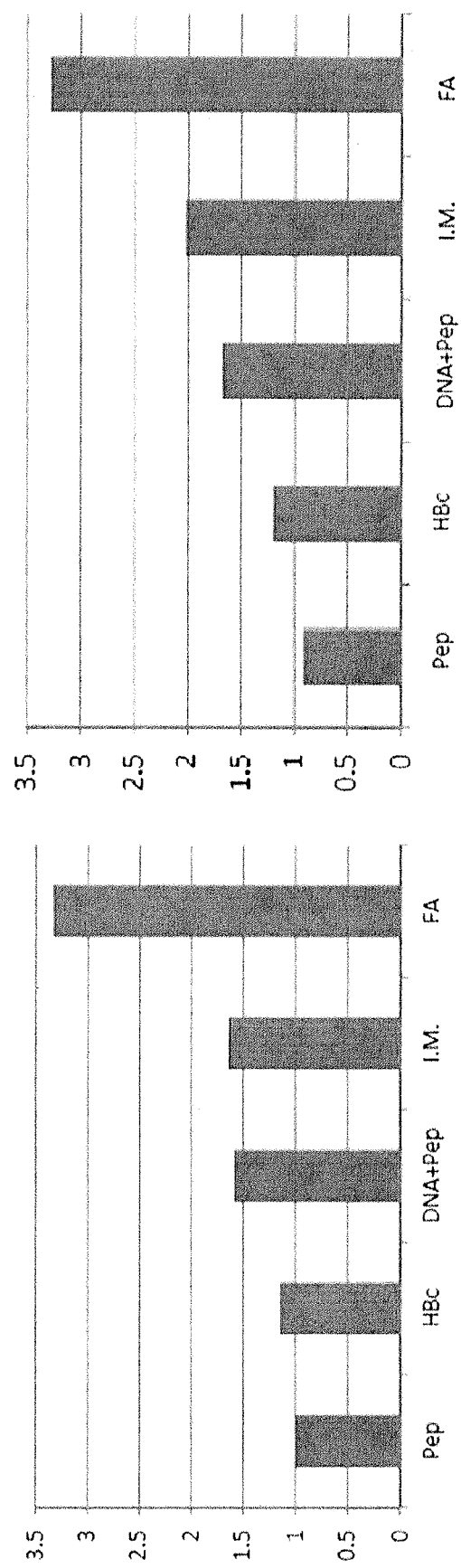
FIG. 7 shows an increase in the antibody titer to angiotensin II by the administration of a vaccine.

The combined use of pcDNA3.1-HBc-AngII and AngII-KLH more remarkably increased the antibody titer to angiotensin II than AngII-KLH single administration. The DNA-peptide combination vaccine was effective not only by ShimaJET® (intradermal administration) but also by intramuscular administration. The increase in the antibody titer tended to last for a longer term with the DNA-peptide combination vaccine than in the peptide single administration group (FIG. 7).

Example 4

Immune Effect of Single Administration of DNA-Peptide Combination Vaccine
(Method)

The immune effect of single administration of the DNA-peptide combination vaccine was studied according to the following protocol.
SHR rat (spontaneously hypertensive rat): n=3
vaccine: pcDNA3.1-HBc-AngII+AngII-KLH
test group
(I) pcDNA3.1-HBc-AngII+AngII-KLH (1 µg) (ShimaJET®, intradermal)
(II) pcDNA3.1-HBc-AngII+AngII-KLH (5 µg) (ShimaJET®, intradermal)
(III) pcDNA3.1-HBc-AngII+AngII-KLH (20 µg) (ShimaJET®, intradermal)
(IV) AngII-KLH (1 µg) (ShimaJET®, intradermal)
(V) AngII-KLH (5 µg) (ShimaJET®, intradermal)
(VI) AngII-KLH (20 µg) (ShimaJET®, intradermal)
All by single administration (on day 0).
evaluation item Time-course changes of the antibody titer to angiotensin II in the peripheral blood were measured.

(Results)

Figure 8:
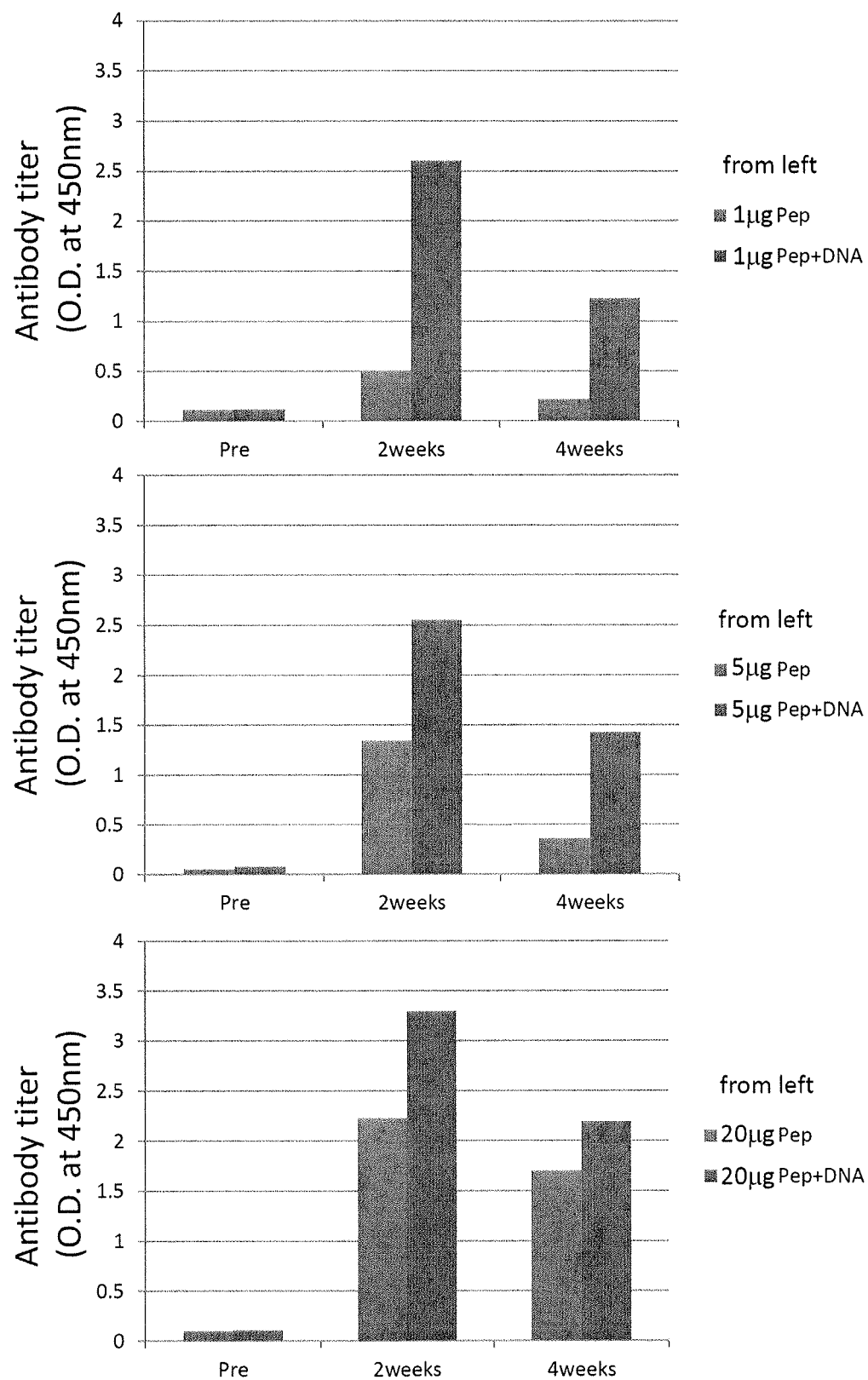
FIG. 8 shows an increase in the antibody titer to angiotensin II by single administration of a peptide vaccine and a DNA-peptide combination vaccine.
Figure 9:
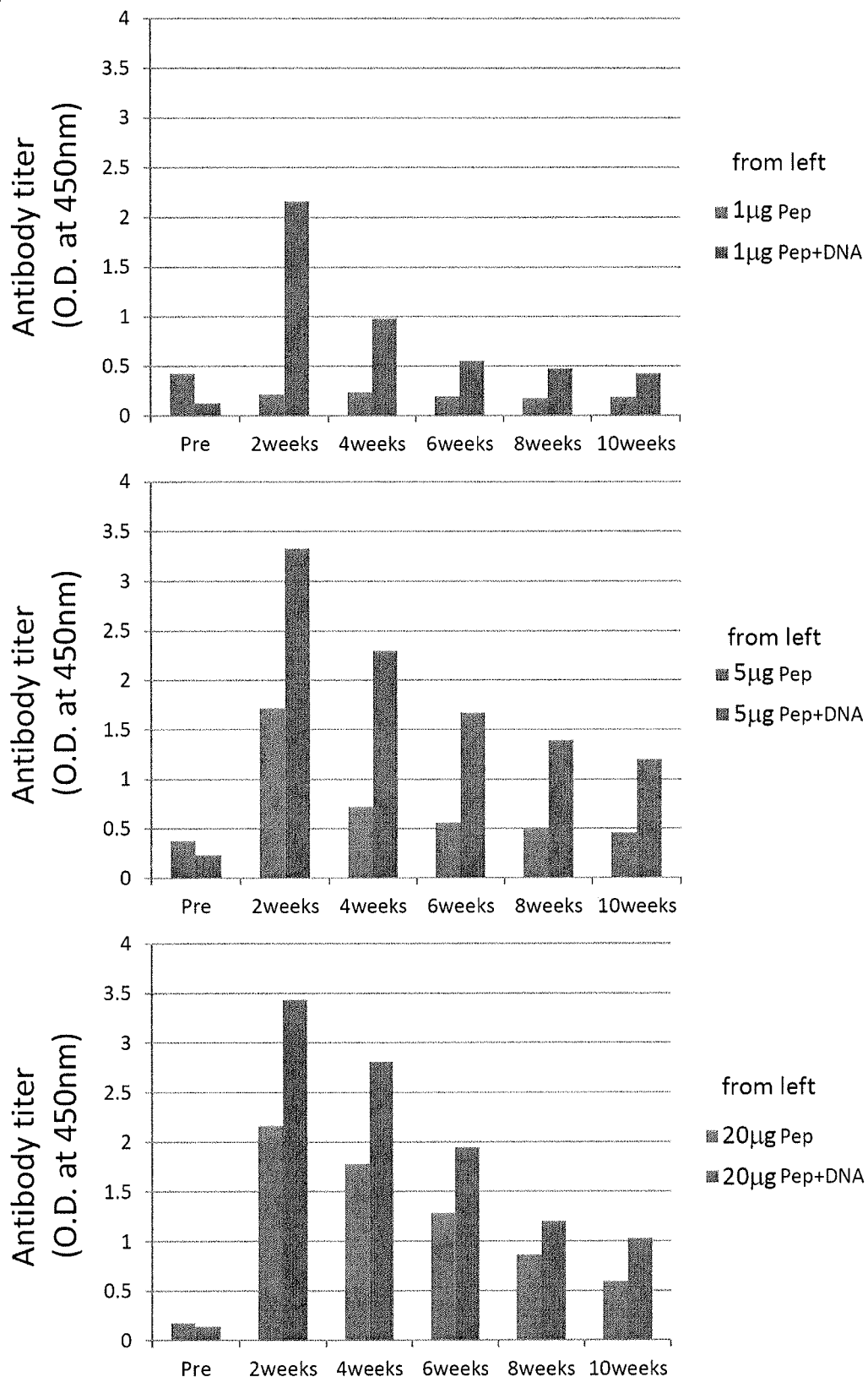
FIG. 9 shows long-term maintenance of an antibody titer to angiotensin II that increased by single administration of a DNA-peptide combination vaccine.
Figure 10:
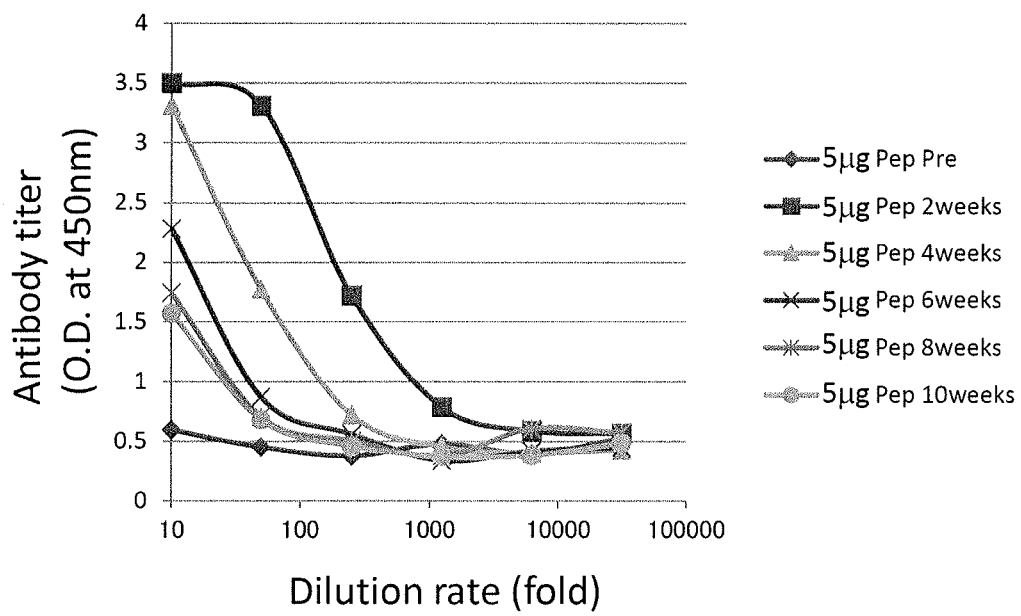
FIG. 10 shows comparison of immunity induction effect by a peptide vaccine and a DNA-peptide combination vaccine under single administration conditions.
Figure 10:
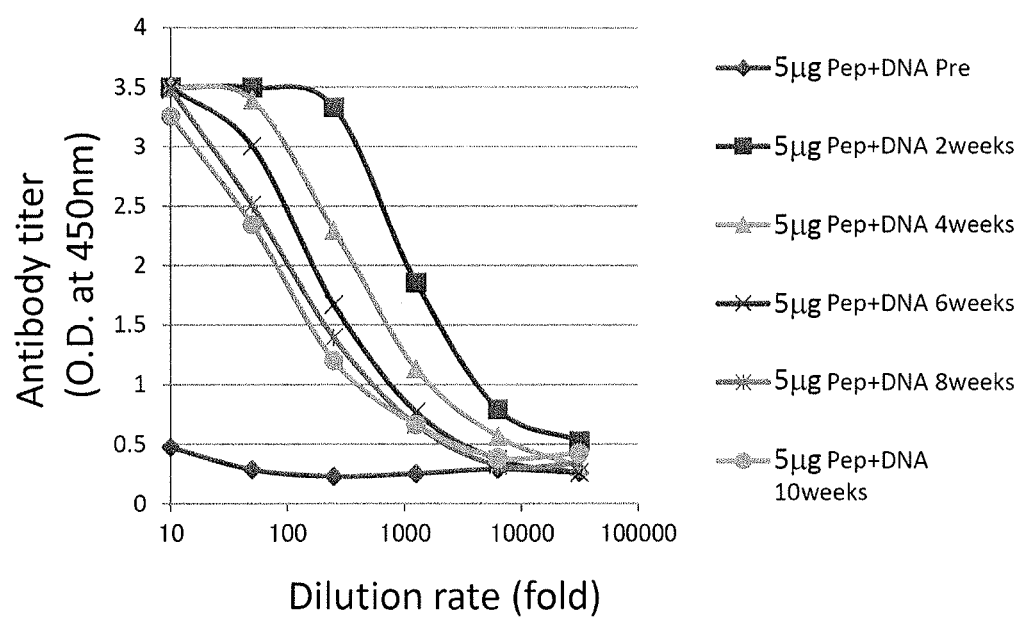

The DNA-peptide combination vaccine showed, even by single administration, a higher increase in the anti-angiotensin II antibody titer than the peptide single administration group. The increase in the antibody titer was maintained for a longer term with the DNA-peptide combination vaccine than in the peptide single administration group (FIGS. 8-10).

Example 5

Immune Effect of DNA-Peptide Combination Vaccine
(Method)
The effect of the DNA-peptide combination vaccine was studied according to the following protocol.
Balb/ca mouse (female, 6-week-old (on the start of vaccine administration)): n=6
vaccine: pcDNA3.1-HBc-mVEGF+-mVEGF-KLH
See WO 2014/034735 A1 for reference.

Figure 11:
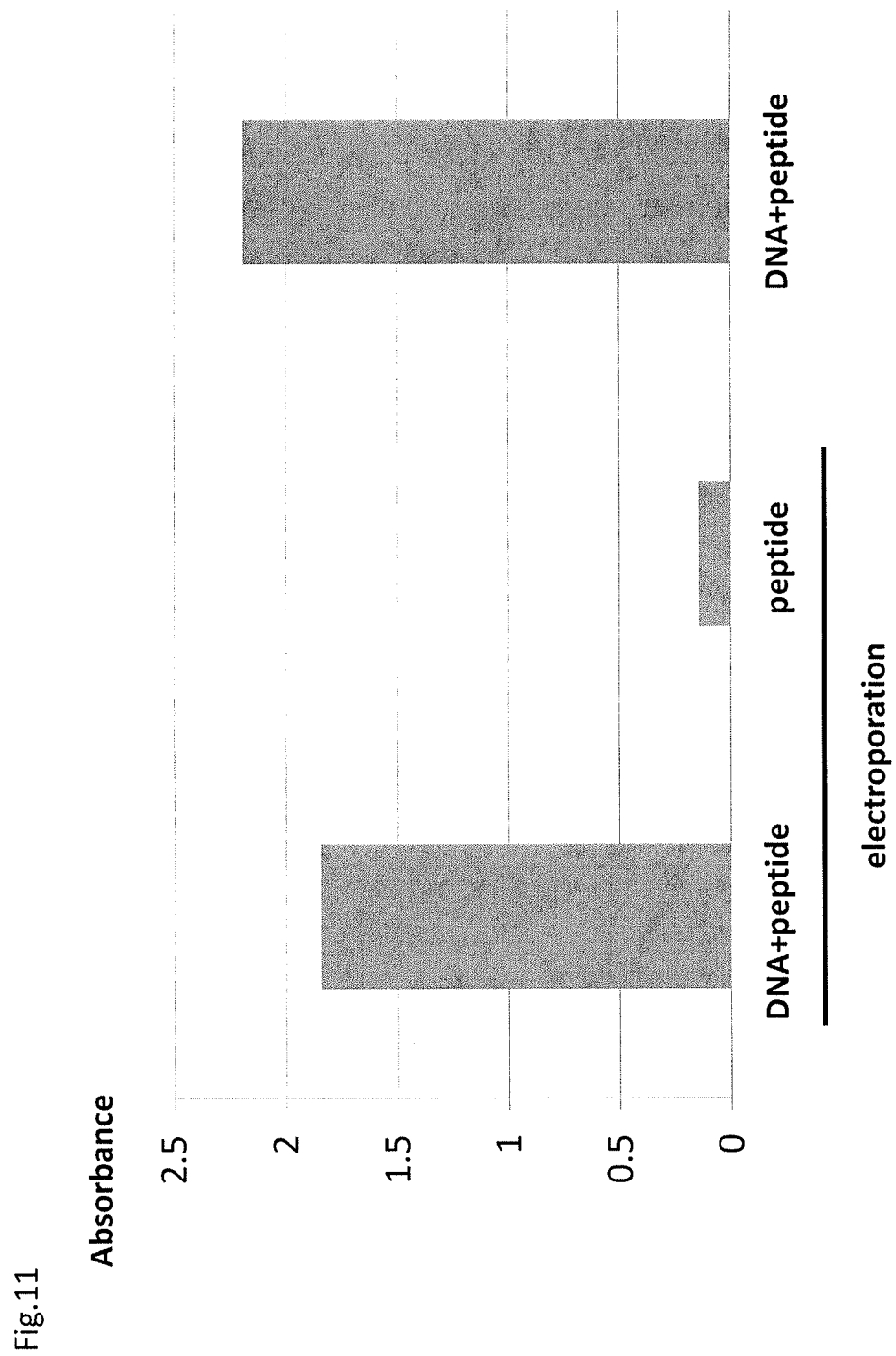
FIG. 11 shows enhancement of immune response by the administration of a DNA-peptide combination vaccine.

```
mVEGF peptide:
                                (SEQ ID NO: 1)
IMRIKPHQSQHIG
``` test group
(I) pcDNA3.1-HBc-mVEGF (2 mg/ml, 60 μl)+mVEGF-KLH (1 mg/ml, 10 μl) (intramuscular administration in legs, each leg 35 μl) (with electroporation)
(II) saline (60 μl)+mVEGF-KLH (1 mg/ml, 10 μl) (intramuscular administration in legs, each leg 35 μl) (with electroporation)
(III) pcDNA3.1-HBc-mVEGF (2 mg/ml, 60 μl)+mVEGF-KLH (1 mg/ml, 10 μl) (intramuscular administration in legs, each leg 35 μl) (without electroporation)
Administered twice in total on day 0 and day 14.
evaluation item
Time-course changes of the antibody titer to VEGF in the peripheral blood were measured.
(Results)
Using the DNA-peptide combination vaccine, the antibody titer to VEGF increased without using electroporation. The group (III) without electroporation showed a higher antibody titer to VEGF than the group (I) with electroporation (FIG. 11).

It was shown from the above results that the use of DNA-peptide combination vaccine can effectively induce a specific immune response to the target antigenic peptide, without using a special apparatus such as electroporation and ShimaJET® (needleless syringe).

Example 6

Figures 1, 12:
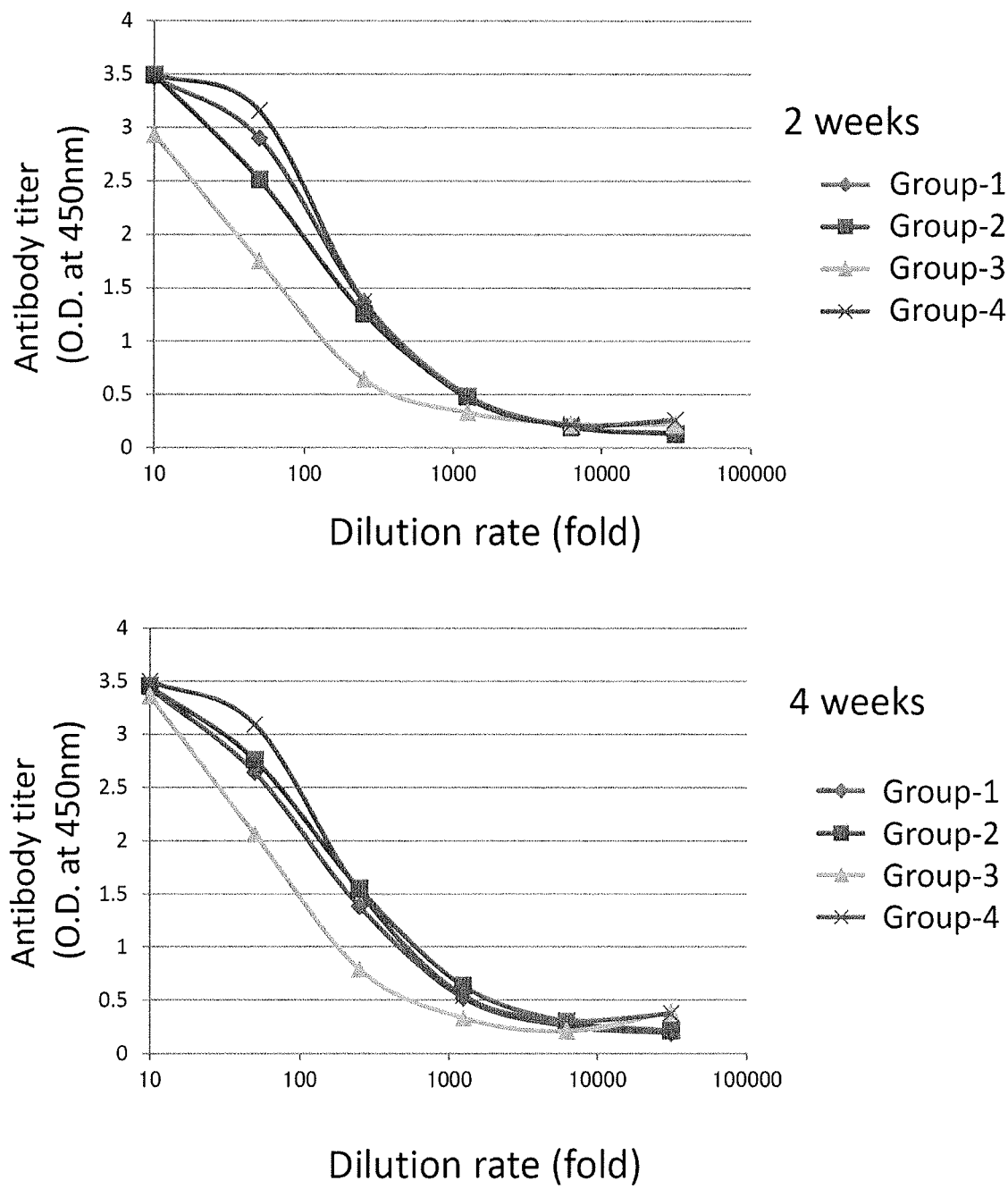
Figures 2, 12:
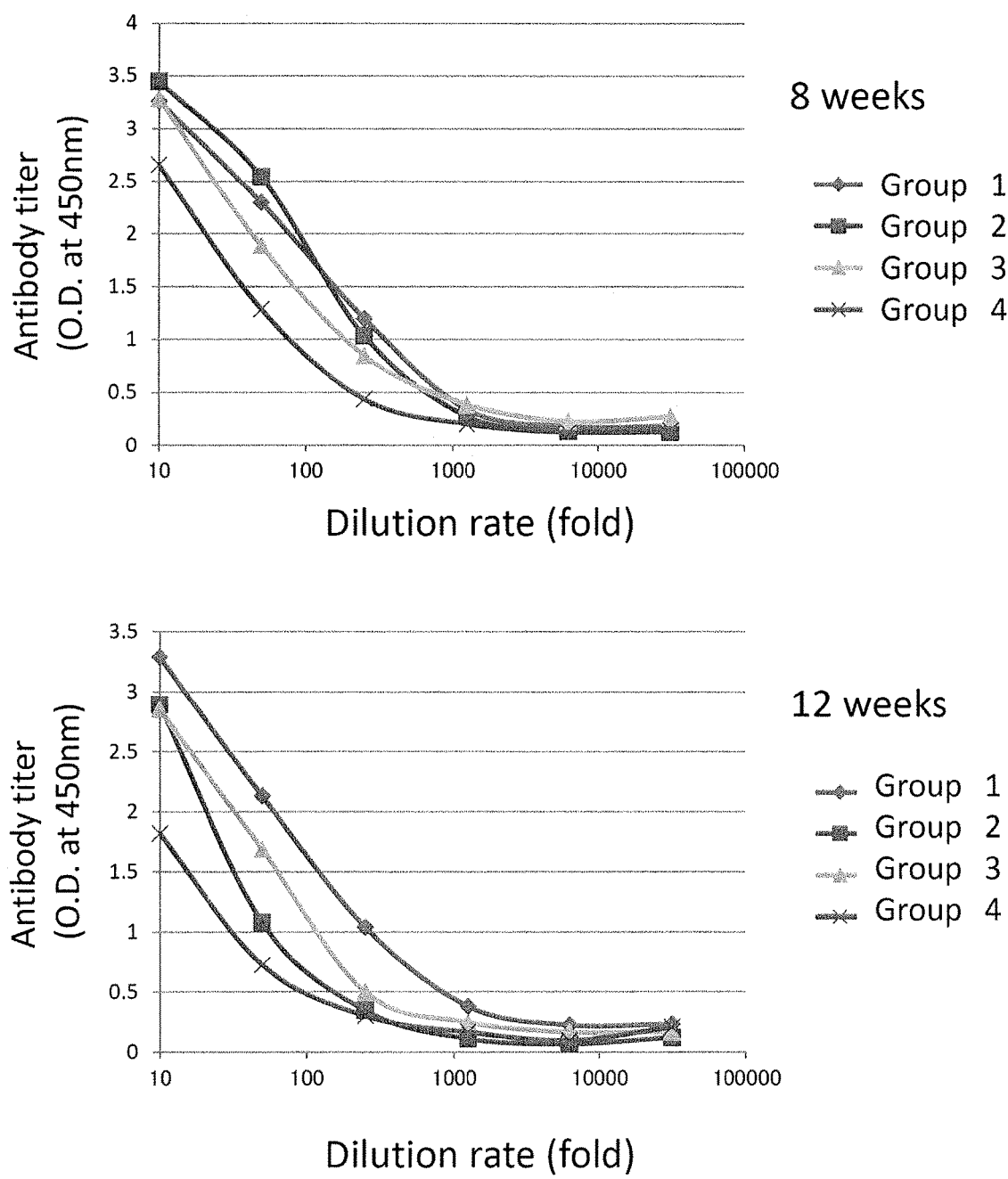
Figures 1, 13:
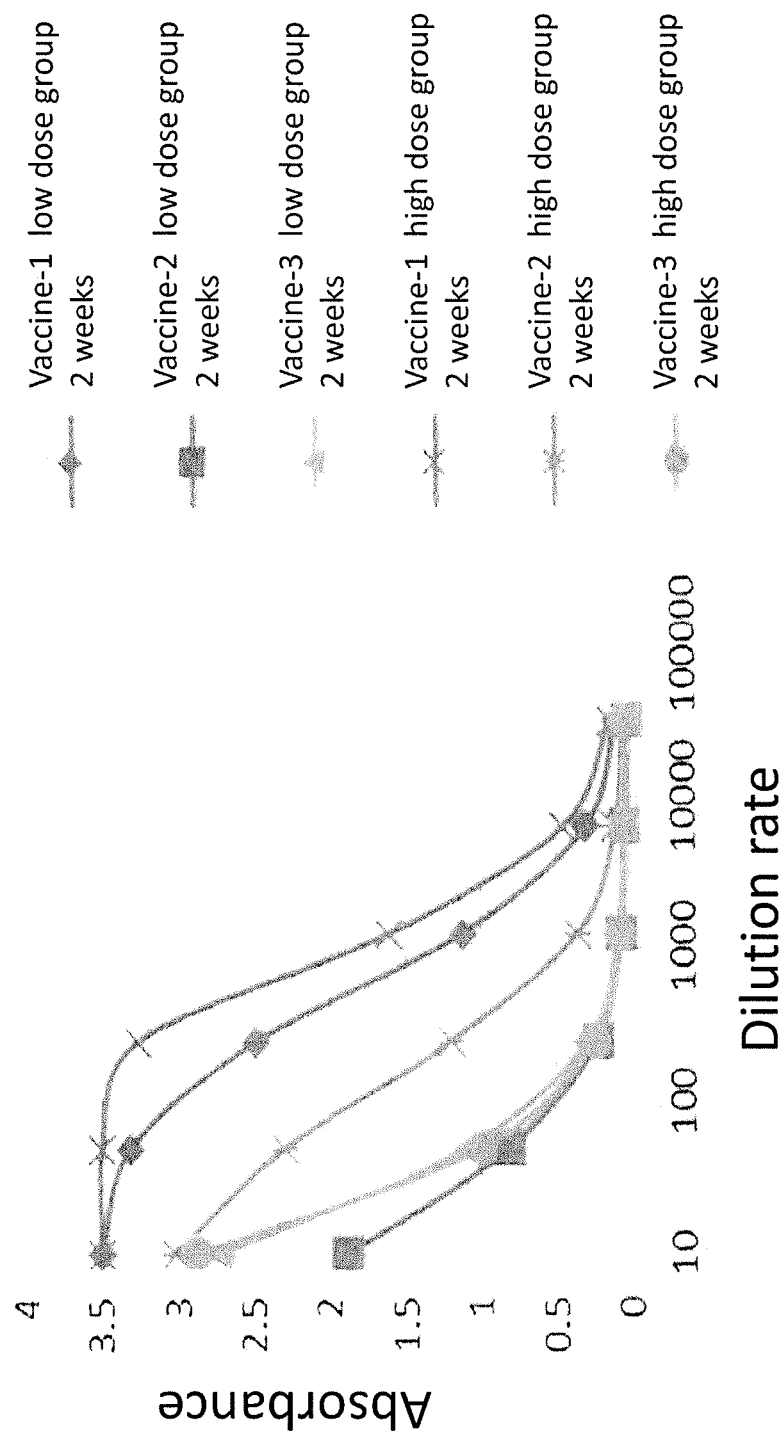
Figures 2, 13:
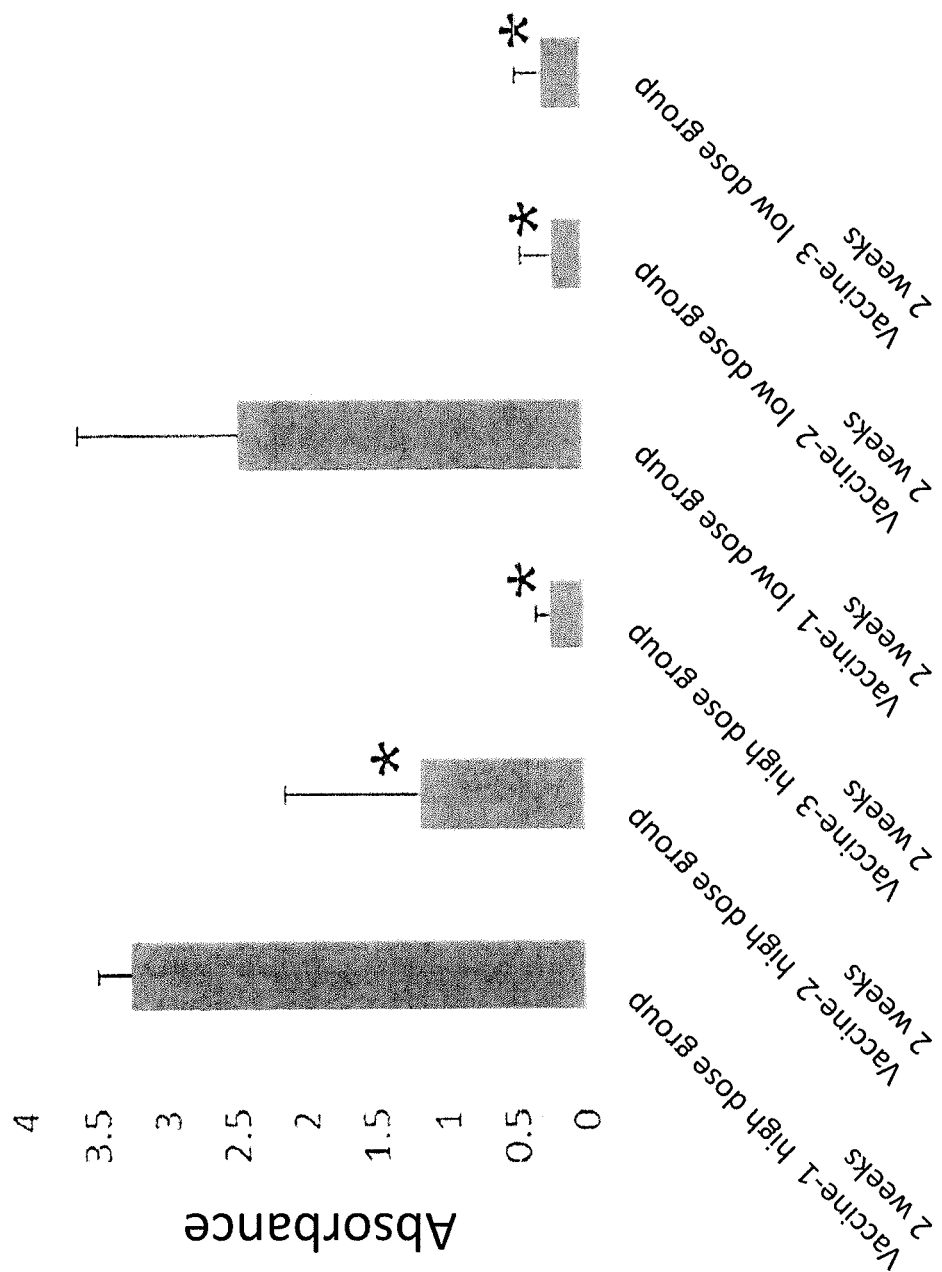
Figures 1, 14:
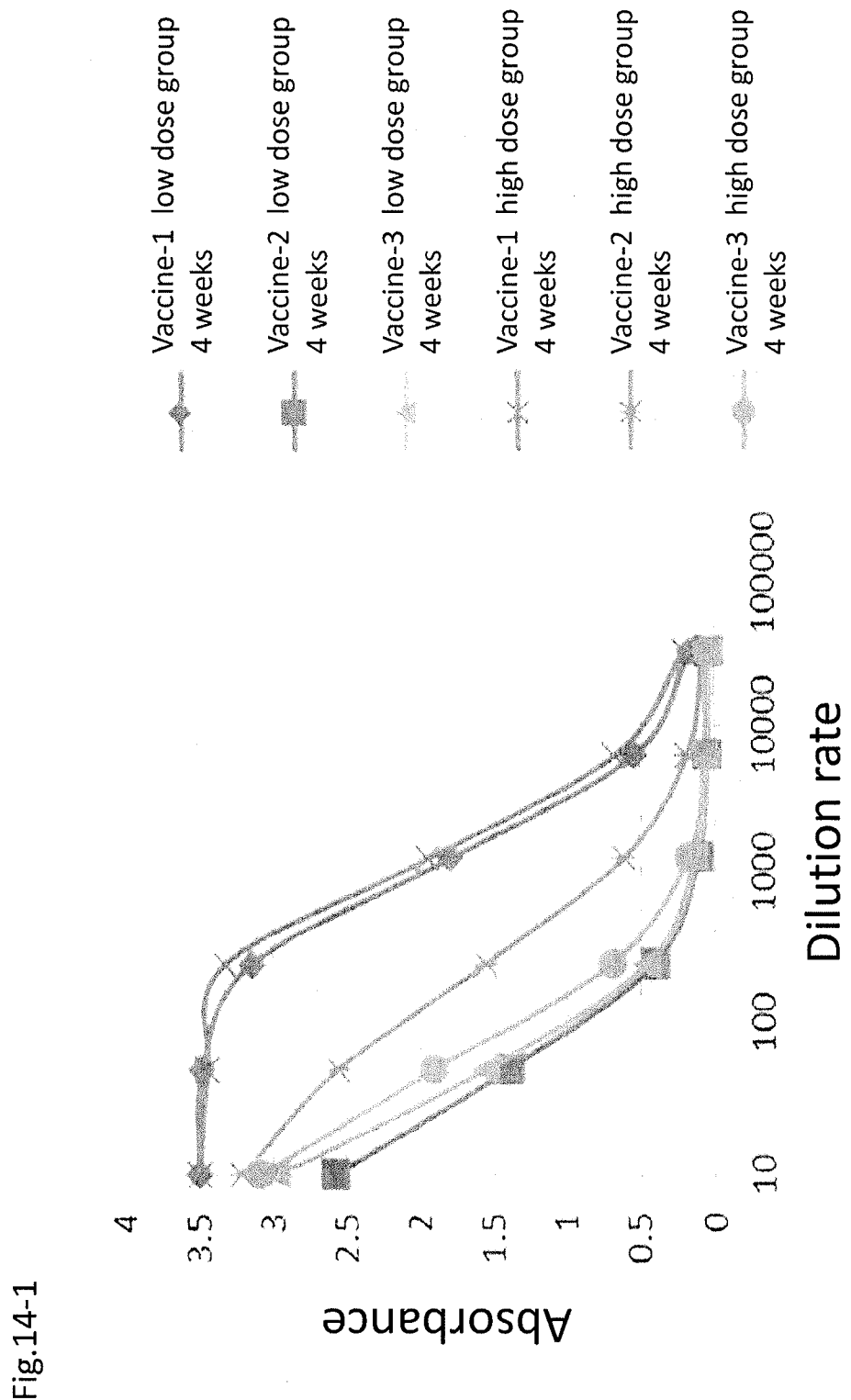
Figures 2, 14:
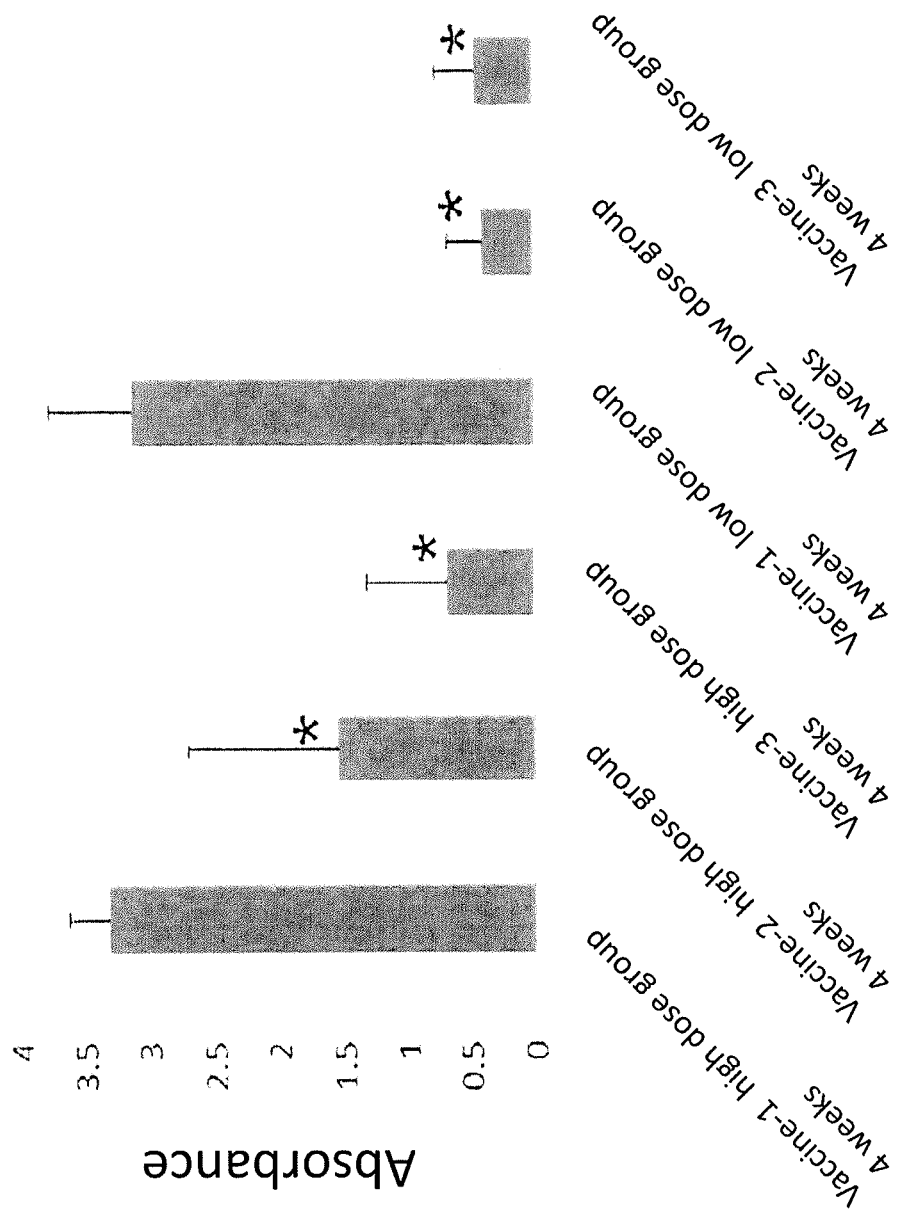

Immune Effect of DNA-Peptide Combination Vaccine
(Method)
The efficacy of pVAX1 vaccine and pcDNA3.1 vaccine was compared according to the following protocol.
SHR rat: n=5-6
In each group, a medicament (200 μl) was intramuscularly administered to the thigh muscle one time, and blood samples were collected on day of administration (immediately before administration), 2, 4, 8, 12 weeks after the administration.
test group
group 1: pcDNA3.1-HBc-AngII (200 μg)+AngII-KLH (5 μg)
group 2: pVAX1-HBc-AngII (200 μg)+AngII-KLH (5 μg)
group 3: pVAX1-HBc-AngII (40 μg)+AngII-KLH (5 μg)
group 4: pVAX1-HBc-AngII (8 μg)+AngII-KLH (5 μg)
evaluation item
The antibody titer to AngII in the peripheral blood was measured.
(Results)
Even when pVAX1 was used as a vector, the DNA-peptide combination vaccine showed an increase in the antibody titer of the same level as the use of pcDNA3.1 (FIG. 12). A possibility of reducing the vector dose to lower than 200 μg was shown. In the early stages (2, 4 weeks) after administration, the antibody titer of each group was not different much; however, it was suggested that a high dose of DNA vaccine maintains a high antibody titer for a longer period.

Example 7

Comparison of Embodiment of AngII Peptide-KLH Conjugate in DNA-Peptide Combination Vaccine
Using three kinds of AngII-KLH conjugates, DNA-peptide combination vaccine was inoculated according to the following protocol, and the effect on antibody titer to angiotensin II in the peripheral blood was compared.
animal used
SD rats (male, 8-week-old (on administration, Japan SLC, Inc.): n=6
test material
(1) test substance 1: angiotensin II vaccine-1
solution containing KLH-AngII conjugate (prepared by glutaraldehyde method) and pVAX1-HBc-AngII (saline).
(2) test substance 2: angiotensin II vaccine-2
solution containing KLH-Cys-AngII conjugate (prepared by Sulpho-GMBS method) and pVAX1-HBc-AngII (saline).
(3) test substance 3: angiotensin II vaccine-3
solution containing KLH-Cys-Gly-Gly-AngII conjugate (prepared by Sulpho-GMBS method) and pVAX1-HBc-AngII (saline).
test substance administration solution concentration

TABLE 1

| administration solution | KLH conjugate | pVAX1-HBc-AngII |
|---|---|---|
| low dose | 0.125 mg/mL (0.025 mg/200 μL) | 1 mg/mL (0.2 mg/200 μL) |
| high dose | 0.5 mg/mL (0.025 mg/200 μL) | 1 mg/mL (0.2 mg/200 μL) | test group
(1) angiotensin II vaccine-1, low dose, n=6.
(2) angiotensin II vaccine-1, high dose, n=6.
(3) angiotensin II vaccine-2, low dose, n=6.
(4) angiotensin II vaccine-2, high dose, n=6.
(5) angiotensin II vaccine-3, low dose, n=6.
(6) angiotensin II vaccine-3, high dose, n=6.
administration
Each vaccine solution was administered singly into the thigh muscle of the rat at a dose of 200 μL/rat by using a polypropylene injection syringe and 27 G injection needle.
blood sampling
(1) blood for plasmid DNA concentration measurement
About 4 hr after test substance administration, blood (about 0.4 mL) was collected from the cervical vein under inhalational anesthesia with 3.0% isoflurane. The blood (300 μL) was collected in a tube added with 100 mmol/L EDTA (60 μL) in advance. The blood was immediately frozen with liquid nitrogen, and cryopreserved at −80° C. until measurement.

(2) serum for antibody titer measurement

On the day before test substance administration, and 2 and 4 weeks after the test substance administration, blood (about 500 μL) was collected into a micro blood-collecting vessel (CAPIJECT, TERUMO, Inc.) from the cervical vein under inhalational anesthesia with 3.0% isoflurane, and centrifuged using a centrifuge (1800 g, room temperature, 10 min) to give serum. The serum was cryopreserved at −80° C. until measurement.

evaluation item (1) antibody titer measurement

The antibody titer to AngII peptide in serum was measured by enzyme immunoassay before the vaccine administration, and 2 weeks and 4 weeks after the administration.

(2) plasmid DNA concentration measurement

The blood plasmid concentration 4 hr after vaccine administration was measured by quantitative PCR. For the quantitative PCR, primer sets with 69 bp as an amplification region, which specifically detects plasmid, was used.

results (1) antibody titer

The antibody titer to AngII peptide in the serum increased in all groups 2 weeks and 4 weeks after the vaccine administration than before the administration. The low dose group and high dose group of angiotensin II vaccine-1 showed significantly high values (p<0.01, FIGS. 13-1, 13-2, 14-1 and 14-2).

(2) plasmid DNA concentration

The blood plasmid concentrations (copies/μL blood) 4 hr after the vaccine administration are shown in the following Table. No group showed a remarkable difference.

administration

Each vaccine solution was administered singly into the thigh muscle of the rat at a dose of 200 μL/rat by using a polypropylene injection syringe and 27 G injection needle.

telemetry transmitter embedding surgery

The rat was anesthetized by intramuscular administration of ketamine hydrochloride and xylazine. The femoral artery was exposed, and a catheter of a telemetry transmitter (TA11PA-C40, DSI) was dwelled in the blood vessel. The main unit of the telemetry transmitter was intraperitoneally dwelled and the wound was sutured.

blood pressure and heart rate measurement measurement period: from one week before vaccine administration (10 days before) to 5 weeks after vaccine administration (35 days later).

measurement items: systolic blood pressure, diastolic blood pressure, average blood pressure, heart rate (calculated from pulse wave of blood pressure)

measurement method: Blood pressure signals sent from the telemetry transmitter embedded in the rat were received by a receiving device (RPC-1, Data Sciences International), and uptaken into a chronic experimental telemetry automatic measurement system (Ponemah Physiology Platform 5.0).

data uptake: Data was uptaken continuously during the measurement period, and the data was preserved at appropriate times.

sampling time: Average of blood pressure and heart rate was calculated every one hour.

TABLE 2

| test group | angiotensin II vaccine-1 | | angiotensin II vaccine-2 | | angiotensin II vaccine-3 | |
|---|---|---|---|---|---|---|
| | low dose group | high dose group | low dose group | high dose group | low dose group | high dose group |
| 1 | $2.14 \times 10^4$ | $5.14 \times 10^3$ | $2.01 \times 10^4$ | $1.54 \times 10^3$ | $1.33 \times 10^3$ | $2.45 \times 10^4$ |
| 2 | $3.50 \times 10^3$ | $3.71 \times 10^3$ | $1.03 \times 10^4$ | $3.40 \times 10^3$ | $6.39 \times 10^3$ | $4.60 \times 10^3$ |
| 3 | $1.15 \times 10^4$ | $2.56 \times 10^3$ | $1.71 \times 10^3$ | $1.15 \times 10^3$ | $1.34 \times 10^3$ | $2.99 \times 10^4$ |
| 4 | $1.12 \times 10^3$ | $3.86 \times 10^3$ | $1.76 \times 10^3$ | $3.59 \times 10^3$ | $2.42 \times 10^3$ | $5.71 \times 10^3$ |
| 5 | $7.27 \times 10^2$ | $4.78 \times 10^3$ | $3.56 \times 10^3$ | $5.53 \times 10^3$ | $2.56 \times 10^3$ | $4.10 \times 10^3$ |
| 6 | $6.22 \times 10^3$ | $2.19 \times 10^3$ | $4.35 \times 10^4$ | $6.22 \times 10^3$ | $4.59 \times 10^4$ | $3.66 \times 10^4$ |
| Mean | $7.41 \times 10^3$ | $3.72 \times 10^3$ | $1.35 \times 10^4$ | $3.57 \times 10^3$ | $9.98 \times 10^3$ | $1.76 \times 10^4$ |
| SD | $7.91 \times 10^3$ | $1.15 \times 10^3$ | $1.63 \times 10^4$ | $2.04 \times 10^3$ | $1.77 \times 10^4$ | $1.45 \times 10^4$ |

Example 8

Effect of DNA-Peptide Combination Vaccine on Blood Pressure of SHR Rat (Measurement by Telemetry)

According to the following protocol, a telemetry transmitter for blood pressure measurement was embedded in SHR/Izm rat, and an influence of the administration of the DNA-peptide combination vaccine on the blood pressure was evaluated.

test schedule

Figure 15:
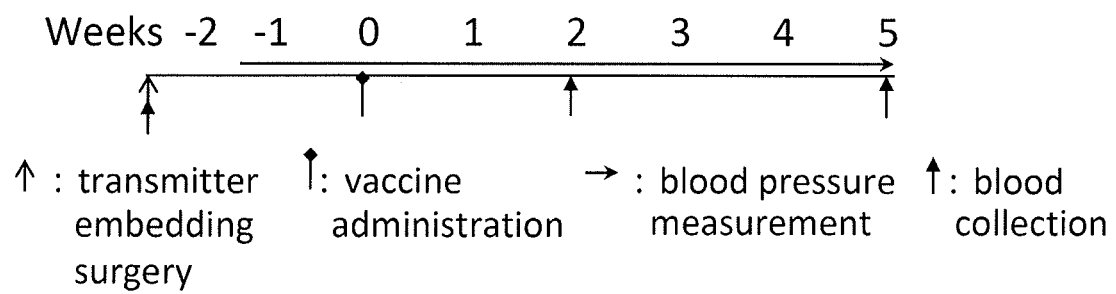
FIG. 15 schematically shows the test schedule of Example 8.

The test was performed according to the schedule shown in FIG. 15.

animal used

SHR/Izm rat (male, 21-week-old (on vaccine administration), Japan SLC, Inc.) 3 rats.

vaccine solution containing KLH-AngII conjugate (50 μg/200 μL) and HBc-AngII expression vector (pVAX1-HBc-AngII: 200 μg/200 μL).

blood sampling blood sampling period: before vaccine administration (on sensor embedding), 2 weeks and 5 weeks after the vaccine administration blood sampling method: Under inhalational anesthesia with isoflurane, a blood sample (about 0.5 mL) was collected from the cervical vein of the rat, placed in a blood collection tube containing EDTA and stirred. The blood was centrifuged (3000 rpm, 10 min, 4° C.) and plasma was collected. The collected plasma was cryopreserved at −80° C.

antibody titer measurement

The antibody titer to AngII peptide in plasma was measured by enzyme immunoassay before the vaccine administration, and 2 weeks and 5 weeks after the administration.

results (1) Effect on blood pressure

Figures 1, 16:
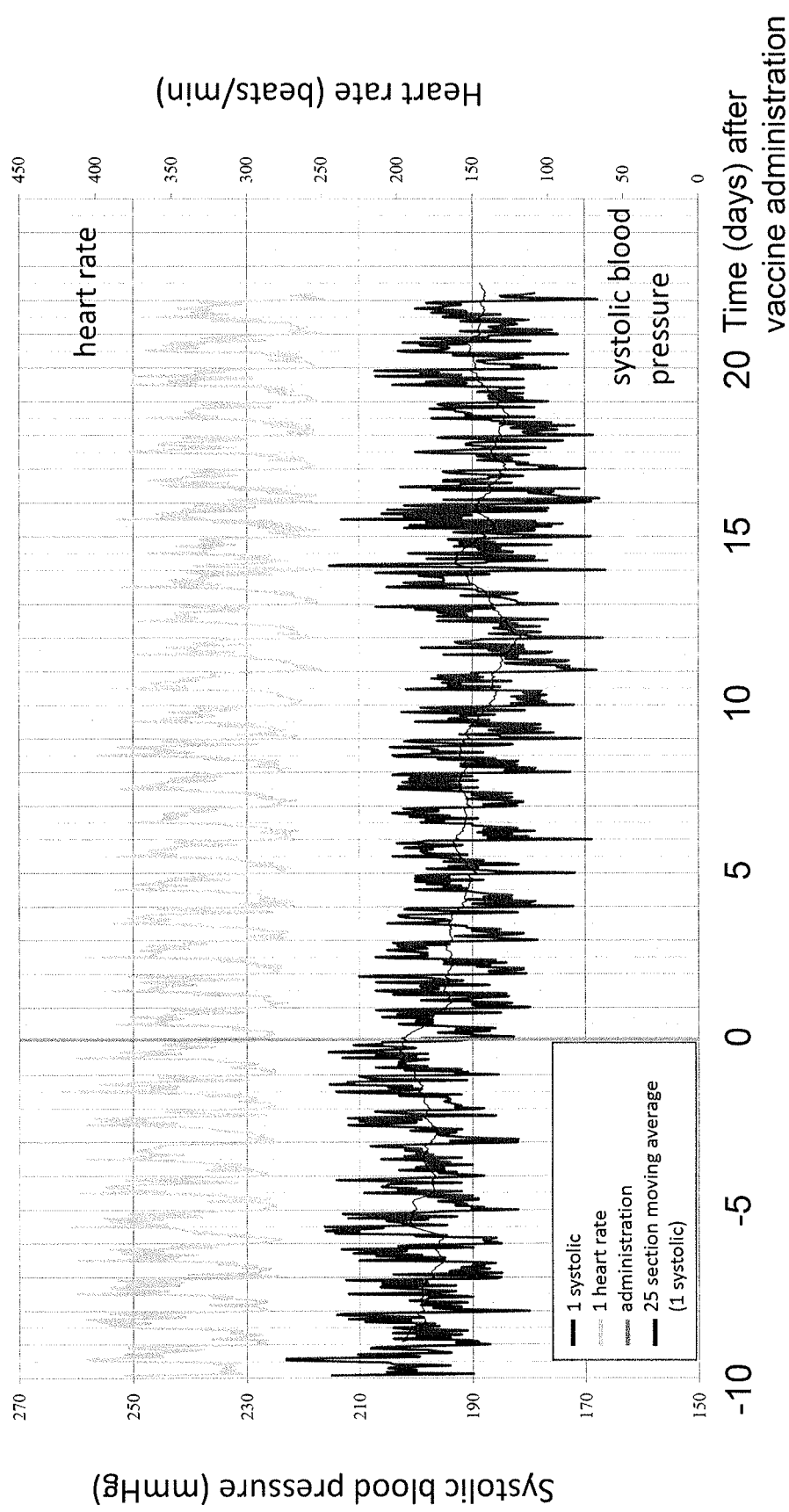
Figures 2, 16:
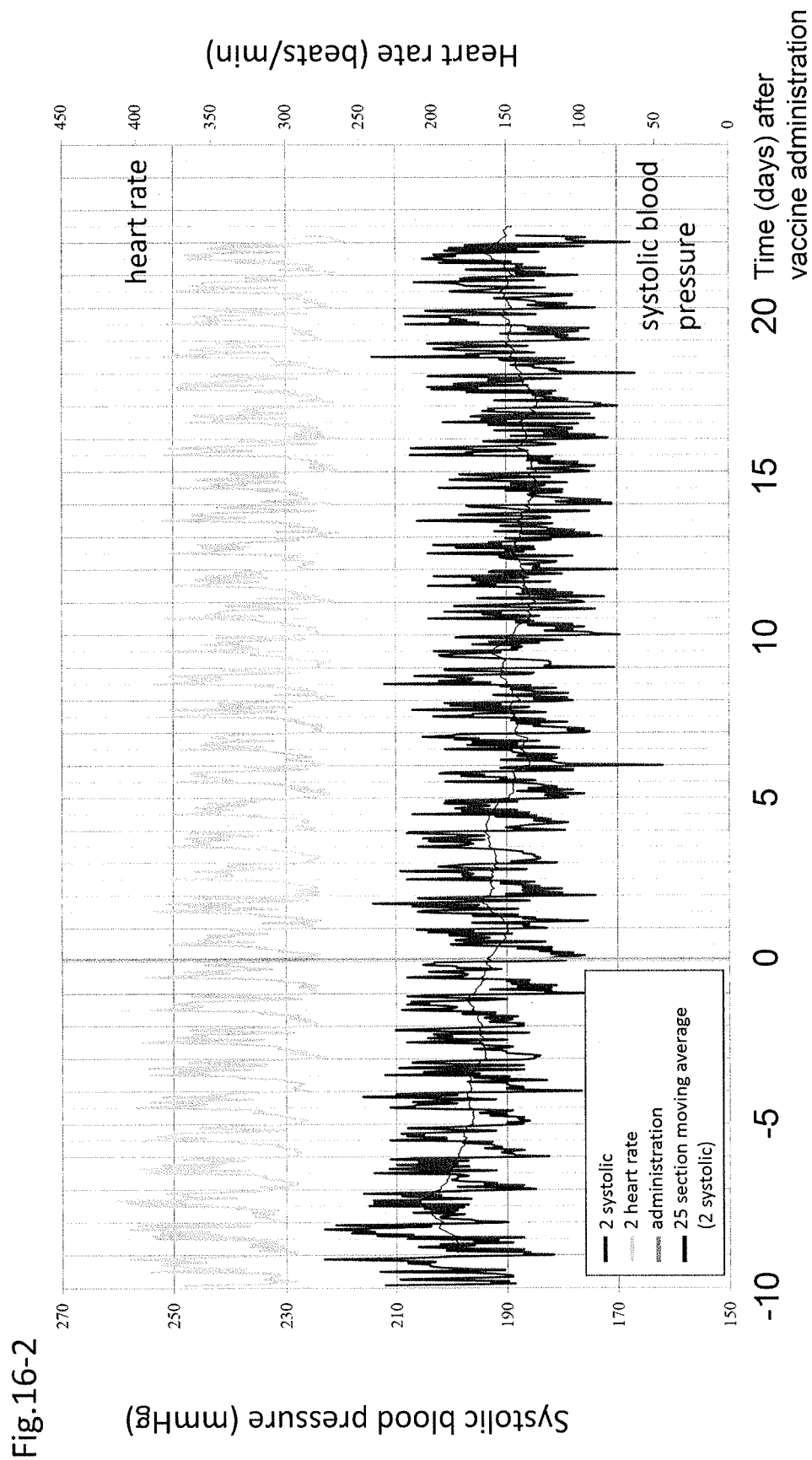
Figures 3, 16:
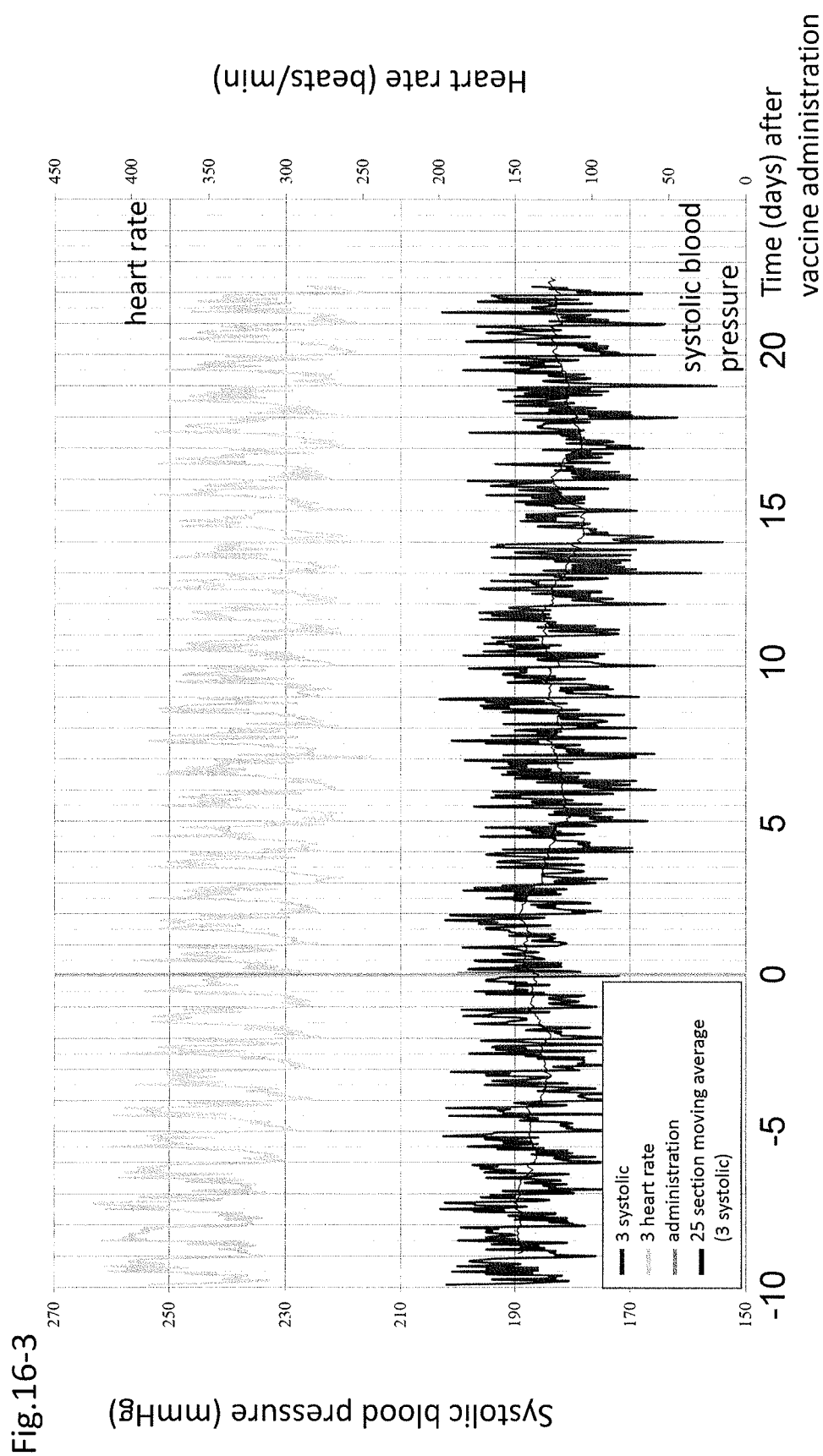

Continuous data of blood pressure and heart rate extracted for 10 min from each animal in the active period (night time) and inactive period (daytime) before the vaccine administration and 2 weeks after the vaccine administration are shown in FIG. 16-1 to FIG. 16-3.

In the animals of No. 1 and No. 2, systolic blood pressure, diastolic blood pressure, average blood pressure, and heart rate decreased significantly by the vaccine administration. Also in the animal of No. 3, a decreasing tendency of systolic blood pressure and heart rate in the active period (night time) by the vaccine administration could be confirmed.

(2) antibody titer

Figure 17:
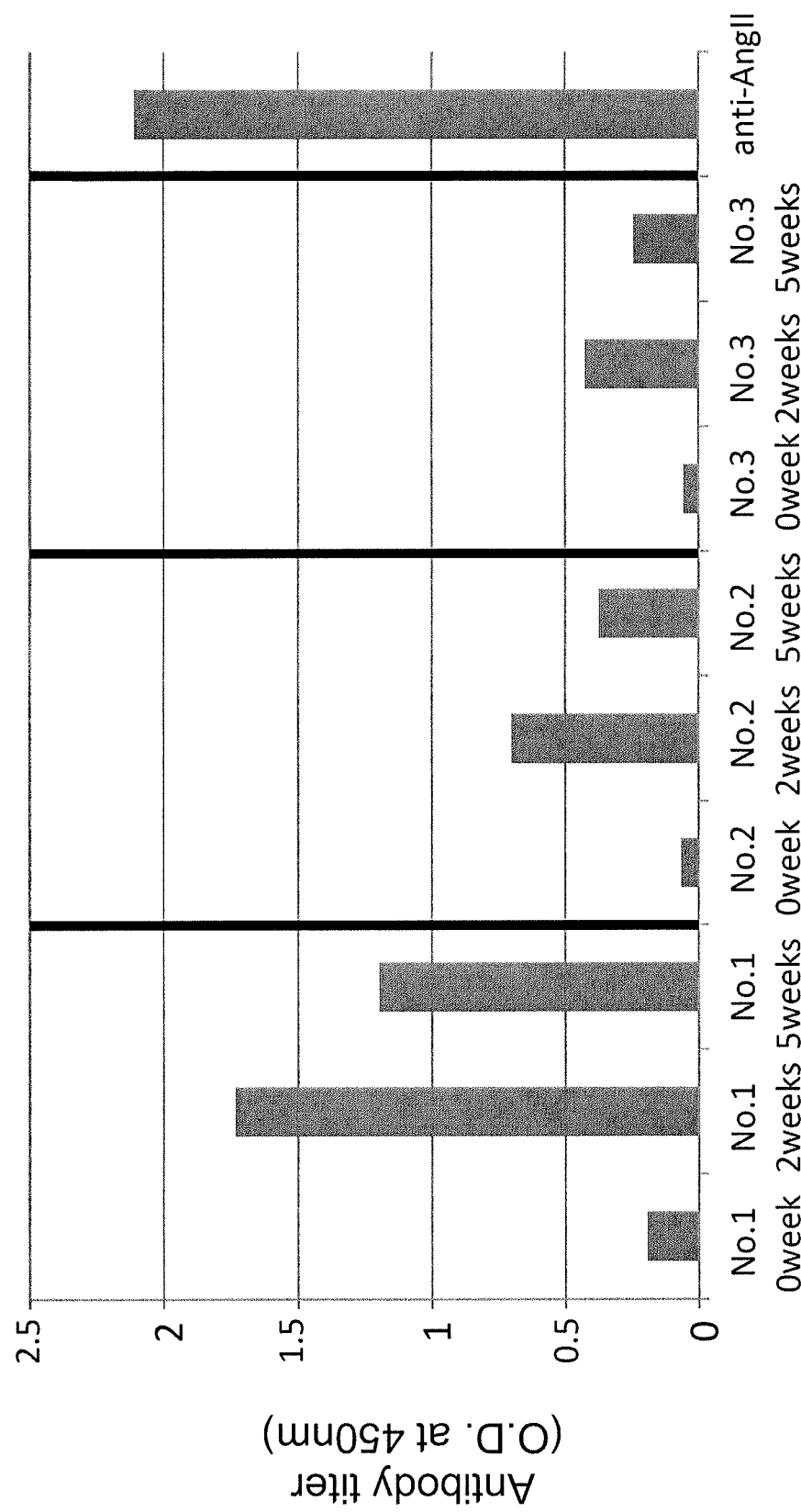
FIG. 17 shows an increase in the antibody titer by the administration of a DNA-peptide combination vaccine (2W and 5W). A 250-fold diluted plasma was used. The vertical axis shows absorbance by ELISA.

The measurement results of antibody titer to AngII peptide (absorbance) by enzyme immunoassay using 250-fold diluted plasma are shown in FIG. 17. In all animals, the antibody titer to AngII peptide increased 2 weeks and 5 weeks after the vaccine administration. In the animal of No. 3 that showed a low blood pressure-decreasing effect, the antibody titer to AngII peptide was also low, and a correlation between the blood pressure-decreasing effect and antibody titer to AngII peptide was observed.

INDUSTRIAL APPLICABILITY

According to the present invention, a vaccine capable of strongly inducing a specific antibody against an antigenic peptide can be provided.

According to the present invention, a specific antibody against an antigenic peptide can be effectively induced using a DNA vaccine, without requiring a treatment such as electroporation, nucleic acid introduction reagent and the like.

According to the present invention, moreover, since an increase in the antibody titer specific to the antigenic peptide lasts for a long term, the number of vaccine administrations can be reduced.

The contents disclosed in any publication cited herein, including patents, patent applications and scientific documents, are hereby incorporated in their entireties by reference, to the extent that they have been disclosed herein.

This application is based on a patent application No. 2014-235736 filed in Japan (filing date: Nov. 20, 2014), the contents of which are incorporated in full herein.

The invention claimed is:

1. A combination for inducing a specific immune response to an angiotensin II peptide in a subject, which comprises
    (I) the angiotensin II peptide consisting of the amino acid sequence of DRVYIHPF (SEQ ID NO: 21), and
    (II) an expression vector encoding a chimeric hepatitis B virus core antigen polypeptide, into which the angiotensin II peptide of (I) has been inserted or added, wherein the angiotensin II peptide of (I) is inserted in a region of amino acid residues 74-87 or 130-138 of the hepatitis B virus core antigen polypeptide, or added to the N-terminal or C-terminal of the hepatitis B virus core antigen polypeptide,
    wherein the angiotensin II peptide of (I) is cross-linked with a carrier protein, and
    wherein the angiotensin II peptide of (I) and the expression vector of (II) are substantially simultaneously administered to the subject.

2. The combination according to claim 1, wherein, in the chimeric hepatitis B virus core antigen polypeptide, the angiotensin II peptide of (I) is inserted between the amino acid residues 80 and 81 of the hepatitis B virus core antigen polypeptide.

3. The combination according to claim 1, which is formulated as a single preparation.

4. The combination according to claim 1, which is free of an adjuvant.

5. The combination according to claim 1, which is for the treatment or prophylaxis of cardiac failure, hypertension, renal failure, arteriosclerosis, myocardial infarction, cerebral infarction, arteriosclerosis obliterans, or dementia.

6. The combination according to claim 5, which is for the treatment or prophylaxis of cardiac failure caused by mitral insufficiency.

7. The combination according to claim 1, wherein the subject is human or a non-human mammal.

8. A method of inducing a specific immune response to an angiotensin II peptide in a subject, which comprises substantially simultaneously administering to the subject one or more times:
    (I) the angiotensin II peptide consisting of the amino acid sequence of DRVYIHPF (SEQ ID NO: 21), and
    (II) an expression vector encoding a chimeric hepatitis B virus core antigen polypeptide, into which the angiotensin II peptide of (I) has been inserted or added,
    wherein the angiotensin II peptide of (I) is inserted in a region of amino acid residues 74-87 or 130-138 of the hepatitis B virus core antigen polypeptide, or added to the N-terminal or C-terminal of the hepatitis B virus core antigen polypeptide, and
    wherein the angiotensin II peptide of (I) is cross-linked with a carrier protein.

9. The method according to claim 8, wherein the carrier protein is Keyhole Limpet Hemocyanin (KLH).

10. The method according to claim 8, wherein the angiotensin II peptide of (I) and the expression vector of (II) are administered in a single dose.

11. The method according to claim 8, wherein the angiotensin II peptide of (I) and the expression vector of (II) are administered by the same administration route.

12. The method according to claim 11, wherein the angiotensin II peptide of (I) and the expression vector of (II) are administered subcutaneously, intradermally, or intramuscularly.

13. The method according to claim 8, wherein electroporation and/or a nucleic acid introduction reagent are/is used for administration of the angiotensin II peptide of (I) and the expression vector of (II).

14. The combination according to claim 1, wherein the carrier protein is KLH.

* * * * *